United States Patent [19]

Moehring et al.

[11] Patent Number: 5,348,015

[45] Date of Patent: Sep. 20, 1994

[54] METHOD AND APPARATUS FOR ULTRASONICALLY DETECTING, COUNTING AND/OR CHARACTERIZING EMBOLI

[75] Inventors: Mark A. Moehring; Mark A. Curry; Merrill P. Spencer; John R. Klepper, all of Seattle, Wash.

[73] Assignee: Applied Physiology and Medicine, Seattle, Wash.

[21] Appl. No.: 947,038

[22] Filed: Sep. 17, 1992

[51] Int. Cl.$^5$ ............................................. A61B 8/06
[52] U.S. Cl. ........................... 128/661.07; 364/413.02
[58] Field of Search .................. 128/661.07–661.09; 73/19.1, 19.01; 364/413.25, 413.02; 604/4, 50

[56] References Cited

U.S. PATENT DOCUMENTS

| 4,152,928 | 5/1979 | Roberts | 73/61 |
| 4,319,580 | 3/1982 | Colley et al. | 128/661 |
| 4,354,500 | 10/1982 | Colley et al. | 128/661.07 |
| 4,434,669 | 3/1984 | Roberts et al. | 73/861.25 |
| 4,673,927 | 6/1987 | Cianciavicchia et al. | 128/DIG. 13 X |
| 5,103,827 | 4/1992 | Smith | 128/661.08 |
| 5,198,776 | 3/1993 | Carr | 128/653.1 X |

OTHER PUBLICATIONS

Moulinier, H. et al "Detecton of Bubbles in Blood Vessels" MBEC vol. 16 Sep. 1978 pp. 585–588.

Primary Examiner—Francis Jaworksi
Attorney, Agent, or Firm—Seed and Berry

[57] ABSTRACT

This disclosure relates to a noninvasive means for detecting, counting and characterizing emboli moving through the arterial or venous circulation. An ultrasonic transducer is applied to the skin or other tissues of the subject at sites such as over the temporal bone on either side of the head of the subject, on the neck, on the chest, the abdomen, arm, leg, within the esophagus, or surgically exposed organs or blood vessels. Using standard ultrasonic Doppler techniques, Doppler-shifted signals are located which are proportional to the blood flow velocity in the blood vessel(s) of interest. Spectral analysis is performed on the received signal using the fast Fourier transform or other appropriate technique to determine the frequency components in the Doppler shift spectrum. Further analysis of the spectra is used to delineate and characterize Doppler shift signals due to blood from Doppler shift signals due to emboli having a variety of compositions.

112 Claims, 29 Drawing Sheets

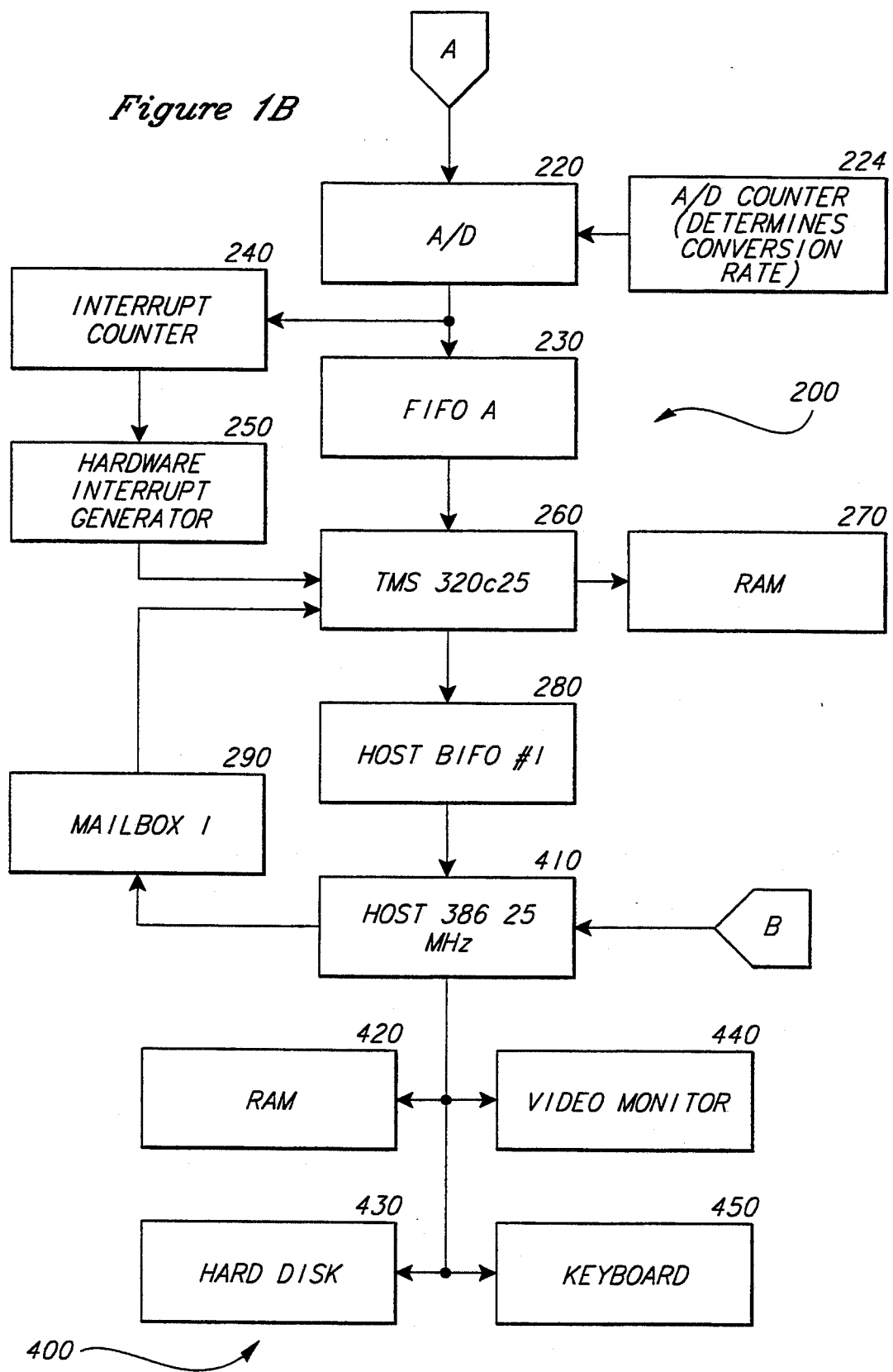

TIMING GENERATOR FOR MULTIPLE DOPPLERS

TIMING DIAGRAM

METHOD AND APPARATUS FOR ULTRASONICALLY DETECTING, COUNTING AND/OR CHARACTERIZING EMBOLI

TECHNICAL FIELD

The present invention relates to human and veterinary medicine and particularly to a method and apparatus to detect, count, size, characterize and indicate the source of emboli, be they particulate or gas, flowing through either the arterial or venous circulation, and is aimed at diagnosing, preventing, minimizing, and treating the source of emboli in these areas.

BACKGROUND OF THE INVENTION

Overview

Emboli may consist of either formed elements such as blood clots, platelet aggregates, or other particulate matter such as pieces of atherosclerotic plaque, fat, or, they may be gas bubbles introduced to the blood vessels through injection, surgical techniques, cavitation at prosthetic valves, or decompression or compression to lower or higher atmospheric pressures. The consequence of arterial emboli may be such pathological conditions as ischemia of an organ or limb, impairment of function, transient ischemic attacks or stroke. The consequence of venous emboli may be pulmonary embolism, pulmonary hypertension, impairment of the function of the heart or lungs or passage to the arterial circulation to produce arterial embolic consequences.

Because the intensity of the ultrasound reflected from emboli exceeding a minimum size is greater than that reflected from normal moving blood, the emboli produce a transient increase in the amplitude of the Doppler shift frequency component corresponding to the velocity component of the emboli parallel to the ultrasound beam.

At present, there exists no other means, either noninvasive or invasive, which allows for the routine dynamic observation and characterization of such transient embolic events.

Prior Ultrasonic Methods

Use of Doppler ultrasound to measure blood flow velocity has been common for many years. The principal of operation is based upon the Doppler shift which provides that ultrasonic signals reflected from moving targets will be detected by a stationary reference transducer with a shift in frequency directly proportional to the flow velocity component parallel to the direction of orientation of the ultrasound beam. This frequency shift due to the Doppler effect is the same for any object moving at a given velocity. The amplitude of the Doppler shift is a function of the acoustic reflectivity of the moving object reflecting the ultrasound.

The magnitude of the reflectivity is a function of the size, shape, orientation, and specific acoustic impedance of the reflector. Most typically for ultrasonic Doppler flow measurement systems, the size of the reflectors, such as red blood cells flowing in whole blood, are very small compared to the wavelength of ultrasound which is used to measure the Doppler shift. In the limit that the reflecting object is small compared to a wavelength, it is generally described as a "scatterer" meaning the ultrasound impinging on the object is reflected nearly uniformly in all directions. In the limit that reflecting objects are substantially larger than a wavelength of the ultrasound used to measure the flow, such objects are described as specular reflectors indicating that the reflection of the ultrasound follows Snell's Law. In this case the ultrasound is reflected in a single specular direction equal to the opposite angle of incidence of the ultrasonic beam. For objects of size in between a pure scatterer and a specular reflector, there is a gradual transition from isotropic scattering (scattering in all directions) to unidirectional specular reflection for objects much greater than a wavelength. Thus, a collection of blood cells clotted together may have very similar specific acoustic impedance to that of a single red blood cell, however, the size of the particle is much larger. This larger size results in an increase in the magnitude of the reflectivity function over that presented by normal flowing blood.

U.S. Pat. No. 4,015,464 to Miller, et al., describes an ultrasonic continuous wave particle monitor which detects the presence of formed element emboli in flowing whole blood in an extra-corporeal device associated with a heart-lung bypass pump. Continuous wave ultrasound is transmitted through a flow-through chamber connected to tubing. Amplitude modulations in the received ultrasound signal are detected as the presence of emboli because of the increased reflectivity of the emboli. This device used transmission ultrasound between two transducers making general noninvasive application of this technique to the animal circulation impractical.

Newhouse (*Journal of the Acoustical Society of America*, 1984) and Li (*Journal of the Acoustical Society of America*, 1992), describe a "pulsed double frequency technique" for detecting and sizing underwater bubbles in the range of 0.5 mm to 1 mm diameter (oceanographic application). This technique uses three transducers, one pulsed and one CW transmitter, and one receiver. The use of three transducers is impractical for animal circulation given the narrow spatial window that is often available for observing vessels. Also, this technique does not detect or characterize formed element emboli.

Features Of Doppler Embolic Signals

The Doppler ultrasonic features of vascular emboli are described in Spencer, Chapter 19, Transcranial Doppler, edited by DW Newell and R Aaslid, Raven Press, Ltd, New York 1992, page 215-230. These features are:

They are short transients less than 0.1 second ranging in amplitude from 3 to 60 dB above the background Doppler blood velocity spectrum.

They are unidirectional within either the advancing or receding velocity spectrum.

Their time duration is inversely proportional to their velocity.

They are random in occurrence in the cardiac cycle.

They are usually changing frequency as they pass through the sample volume.

They sound to the ear like harmonic chirps, whistles, moans or clicks depending on their velocity.

In contrast, artifactual transients, defined as noise transients, are represented by:

Energies weighted in the low-frequency range.

The energy spread into higher frequency ranges when louder or stronger.

They are bidirectional as they spread away from zero frequency reference.

They are coincident with probe impacts, sudden motion or electrical switching transients.

The auditory effect is that of noise rather than the tonal quality of embolic signals.

In the case of detection of a gas embolism flowing in blood, the reason for the increased reflectivity of ultrasound can be related to the large difference in specific acoustic impedance between that of the gas and that of whole blood. Detection of such gas bubbles in the human circulation was first reported by Spencer, et al., (*Journal Occupational Medicine,* 1969). This technique was further refined to detect arterial embolism during open heart surgery, Spencer, et al, (*Annals of Thoracic Surgery,* 1969), and has been used as a means for quantitating decompression sickness by counting the number of gas emboli passing through the pulmonary artery, Spencer, et al, (*Aerospace Medicine,* 1972); Spencer, et al, (*Cardiovascular Applications of Ultrasound,* 1974); and Spencer, (*Journal of Applied Physiology,* 1976). As described in these articles, gas emboli are represented in the Doppler ultrasound signal as short transient events characterized by short whistles or chirps which are easily heard by ear in the Doppler audio signal. The Doppler audio characteristics of these passing bubble emboli are described by the features previously listed and signify gas bubbles moving along with the blood flow such that the signal presented is an increase in amplitude or loudness of a particular tone representing the velocity of a single highly reflective particle passing through the ultrasound beam.

As a means for further analysis of these signals, spectral analysis has been applied to the signals received from gas emboli in the pulmonary artery by Kisman, (*Ultrasonics,* 1977).

Further algorithms were developed and tested to quantify the number of bubbles formed during decompression, Belcher, (*IEEE Transactions on Biomedical Engineering,* 1980). Belcher's method divided the Doppler spectrum into a series of discrete bands in frequency. A baseline average amplitude was determined in each of these bands by averaging signals over a period of several minutes when no bubbles were present. A threshold was set for each of these bands, above which signal was counted as a bubble if the signal exceeded the threshold in only one band or in two adjacent bands. If the signal exceeded the threshold in more than one band during one time sample, it was assumed to be noise since broad band signals may be associated with transducer motion, valve clicks, heart wall motion, or electronic interference.

Limitations Of Previous Ultrasound Methods

Amplitude and threshold recognition of embolic signals is basic and previously applied but is insufficient for reliable recognition and detection of intravascular emboli. Among the problems with amplitude only detection are limitations of dynamic range of the FFT, the Doppler audio electronics and the tape recorders, as well the false recognition of probe impact and other electronic switching transients.

While use of a standard Doppler apparatus may be adequate to allow for detection of emboli, reliable differentiation from artifacts and characterization of such emboli concerning their composition and size with such an apparatus cannot, in general, be accomplished unless some a priori information is available from another source. The amplitude of the Doppler shift signal alone does not provide unambiguous delineation, since, for example, the amplitude of Doppler signal produced by a small bubble may be equal to the amplitude produced by a larger solid embolus. In a surgical procedure where potentially both solid and gaseous emboli may be present, such delineation may be important.

Clinical Recognition And Limitations

Currently the only routinely used means for determining that emboli may be flowing through the arterial circulation is indirect, through the observation of the pathological consequences of such emboli lodging in the end arterial vessels producing ischemic regions in the brain, abdominal organs or extremities. Such ischemia may eventually produce regions of infarct or tissue death that result in permanent functional deficits. Currently a device to provide prior warning of such permanent deficits is not available. Ophthalmoscopic examination of the retinal surface or fundus photography can identify emboli lodged in the retinal arteries and if identified as a Hollenhorst plaque, identifies the character of their origin but these are usually identified after an episode of blindness as noted by the subject seeking attention from a physician.

The presence of an embolus may be detected indirectly through x-ray angiography. Vessels which have been occluded or severely stenosed by the presence of a stationary blood clot may be evidenced in the x-ray image by either poor visualization or lack of visualization of particular vessels in the brain or other organs. X-ray computed tomography and magnetic resonance imaging may be used to demonstrate regions of infarct created by cerebral ischemia caused by emboli lodged in the supplying arterial vessels. However, these methods produce only images of the end result of such emboli and cannot image the embolus directly.

Thus, there exists a need for a noninvasive technique for the detection and quantification of emboli that may be flowing through the circulation. Such a device would determine the passage of transient emboli. Particularly needed is a method and device to detect microemboli of sufficiently small size that overt clinical signs are not yet recognized but which may be breaking off from a source of potentially great size and clinical consequence, or of clinical consequence by accumulation over time. This may be useful in determining the course of therapy for the patient, which may be either by surgery or medication, and may also provide an indication of treatment results. Likewise, the cause of a stroke or transient ischemic attack may be inferentially determined by the presence [or absence] of such emboli. For example in patients with symptoms of cerebral vascular insufficiency, the finding of microemboli may indicate the etiological source of the symptom producing large embolus.

The source of arterial emboli may be indicated by sequential or simultaneous monitoring along the vasculature with multiple probes. Convenient locations for interrogation of brain supplying arteries include the common carotid arteries, the cervical internal carotid arteries, and the middle cerebral arteries. Other arteries may be used such as the subclavian, vertebral, basilar or ophthalmic arteries.

For example, when emboli occur frequently from a prosthetic valve source in the heart, sequential or simultaneous monitoring can specify the source as the heart or aortic arch by the presence of bilateral microemboli in both common, internal or middle cerebral arteries. In patients in whom multiple emboli are detected only unilaterally in the cervical internal carotid artery and not in the homolateral common carotid artery, the source may be specified at the bifurcation of the common carotid artery. Similarly, when detected in the middle cerebral artery and not in the cervical internal carotid artery, the source may be specified in the siphon component of the internal carotid artery.

Similarly the source of emboli may be indicated by regional monitoring of the arterial or venous tree throughout the body at multiple sites. In the case of venous microemboli which frequently arise from the veins of the lower extremities, microemboli may be detected at multiple sites along the veins of the lower extremities or in the inferior vena cava.

SUMMARY OF THE INVENTION

The primary object of the invention is to provide an accurate real time Doppler ultrasound system for detecting the presence of microemboli in blood flow, and to further characterize such emboli by probable number, composition and size.

This and other objectives of the invention are provided by an ultrasound transducer positioned adjacent the blood flow so that the transducer is in ultrasound communication with the blood flow. A Doppler ultrasound unit is electrically connected to the ultrasound transducer to generate an output signal having a frequency spectrum indicative of the velocity of ultrasound scatterers in the blood flow. A signal processor determines a frequency spectrum corresponding to the output signal, and then detects the presence of an embolus in the blood as a function of a relationship between the amplitude of at least two frequency components in the frequency spectrum. The processor also preferably provides an indication of an embolus if the amplitude of at least one frequency component, and preferably an average of the amplitudes of a plurality of adjacent frequency components, exceeds a threshold. The processor preferably detects an embolus only if the amplitude of one frequency component is greater than a threshold and the amplitude of a second frequency component is less than a threshold. The processor preferably detects an embolus only if the number of times that the amplitude of one frequency component in each pair has a predetermined relationship to the amplitude of the other frequency component in the pair more than a predetermined number of times. Also, the processor preferably detects the embolus only if the frequency components in a spectrum exceed a threshold. The processor may also include means for determining if an artifact is present and for inhibiting the detection of an embolus in such circumstances.

The inventive method and apparatus may also determine a characteristic of an embolus, such as its size or composition, either alone or in connection with the detection method and apparatus. If so, a plurality of Doppler ultrasound units are electrically connected to the ultrasound transducer. Where a pulse Doppler ultrasound units are used, they operate at different carrier frequency but has the same pulse duration, pulse repetition rate, and depth gate. A signal processor then determines a characteristic of a detected embolus as a function of a relationship between a characteristic (e.g., power) of the frequency spectrum in the output signal from one pulse Doppler unit and a characteristic (e.g., power) of the frequency spectrum in the output signal from another Doppler unit. The processor preferably operates by determining a set of first intermediate values each of which corresponds to the power of the frequency spectrum from a respective Doppler unit indicative of ultrasound reflected from blood and emboli, then determining a set of second intermediate values each of which corresponds to the power of the frequency spectrum from a respective Doppler unit indicative of ultrasound reflected from blood alone, and then calculates a set of composite values each of which is a function of the first and second intermediate values determined from the same Doppler unit. The characteristic of the embolus can then be determined as a function of a relationship between at least two of the composite values in the set. Each of the sets preferably contain three values, and a characteristic of the embolus is identified as a function of both a relationship between two of the composite values and the relationship between one of the two composite values and the remaining composite value. The first composite value is preferably determined from a first Doppler unit having the highest carrier frequency, the third composite value is preferably determined from a third Doppler unit having the lowest carrier frequency, and the second composite value preferably determined from a second Doppler unit having a carrier frequency that is intermediate the carrier frequencies of the first and third Doppler units. The processor preferably scales the frequency of the components in the spectra for two of the Doppler units as a function of the relative carrier frequencies of the Doppler units so that the Doppler frequencies of the Doppler units are scaled to the same value responsive to scatters in the blood moving at the same velocity.

DETAILED DESCRIPTION OF THE INVENTION

Overview

Figure 1A:
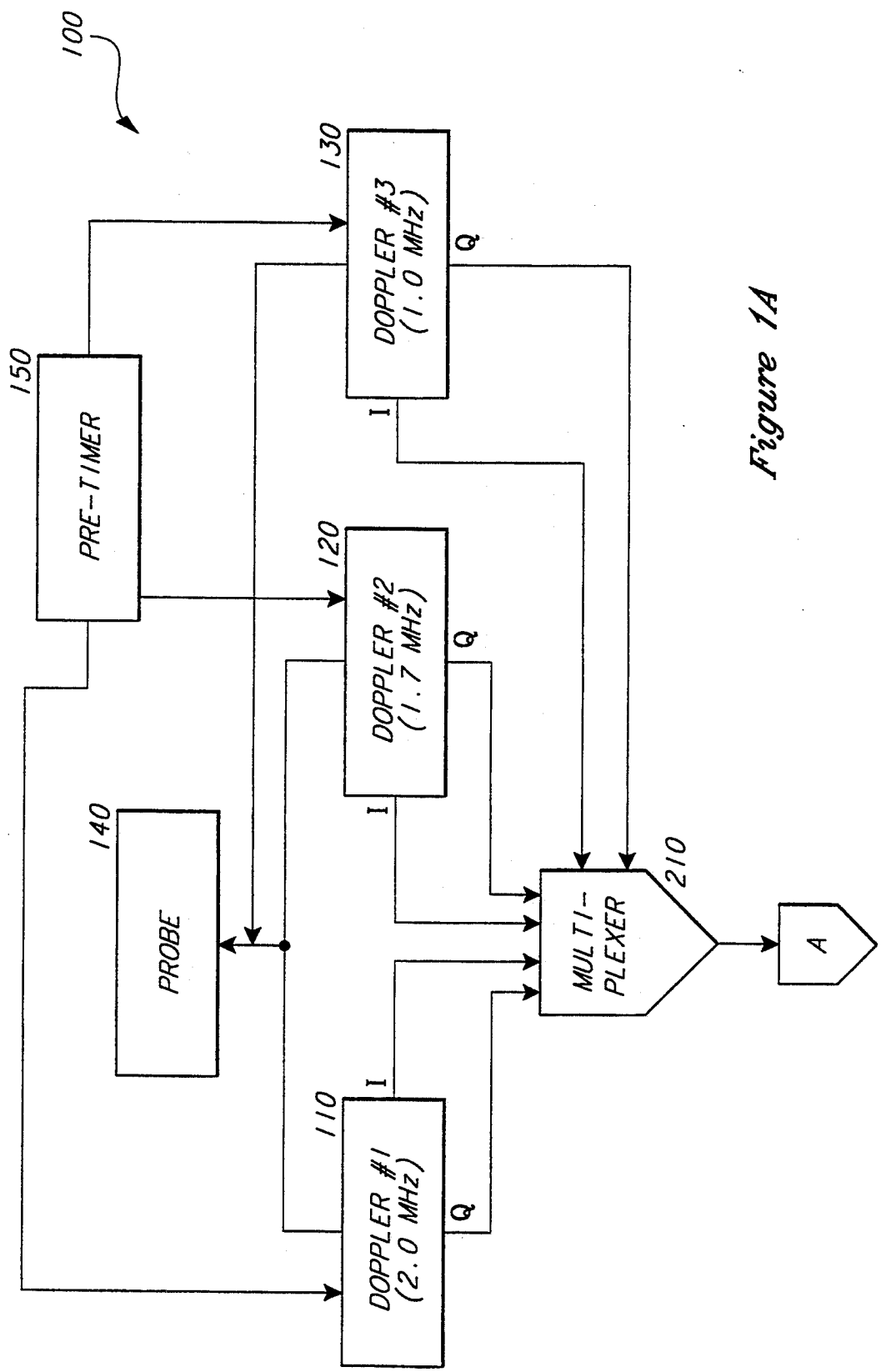
FIG. 1 is a block diagram of a preferred embodiment of the inventive system.
Figure 1C:
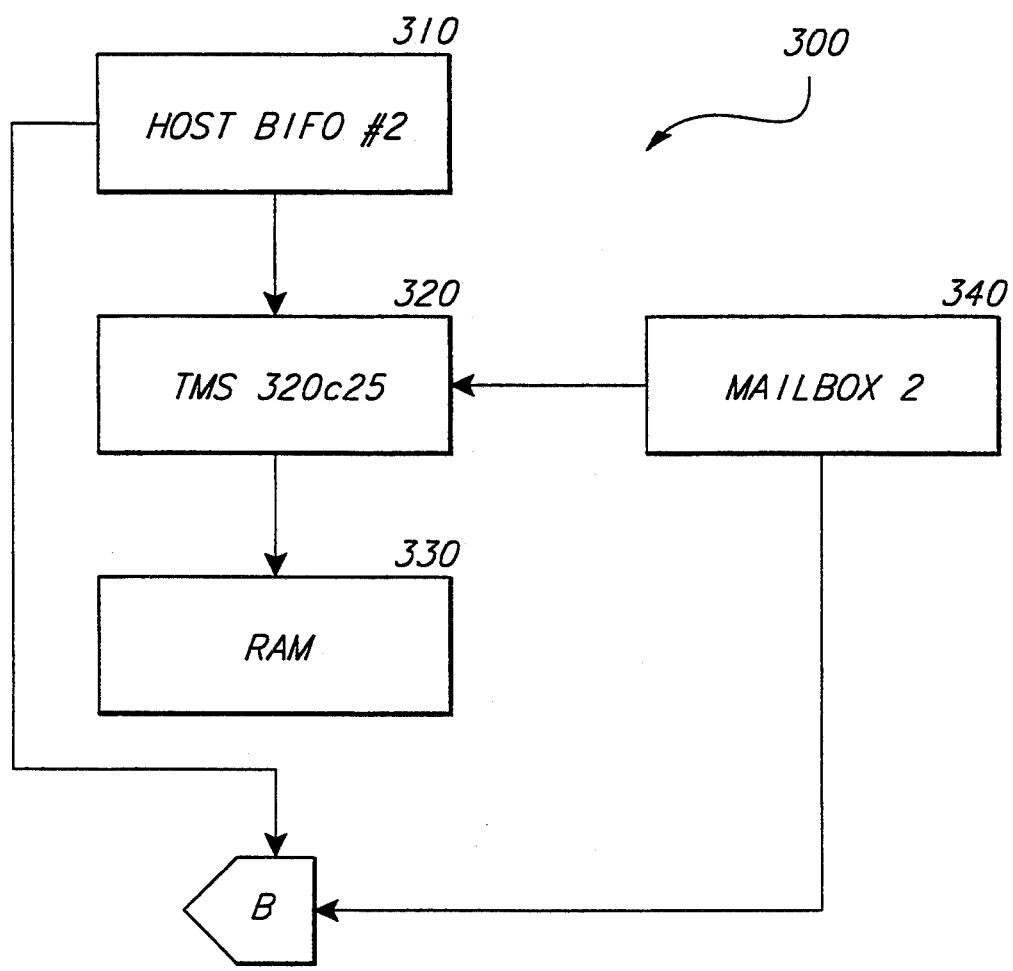

The system architecture for one embodiment of the invention is shown in FIG. 1. The system contains a pulse Doppler section 100, a digital signal processor section (DSP) 200, a second DSP section 300, and a Host computer 400.

The pulse Doppler section 100 transmits an ultrasonic pulse to the vessel under study, receives the echoed pulse, and processes Doppler shift signals due to the blood or blood plus embolus moving within the vessel. As shown in section 100, three conventional Doppler units (110, 120, 130) are used. Each Doppler unit transmits a pulse centered about a unique carrier frequency, and the transmitted pulses have the same time duration. The same sample volume is interrogated by each Doppler unit. The same transducer 140 is used to generate the ultrasonic pulse for each Doppler unit. The pulse repetition for each Doppler unit is caused by the same clocking circuit 150, causing the pulse repetition frequencies (PRFs) of the three Doppler units to be identical.

The first DSP section 200 digitizes the analogue Doppler shift signals from the three Doppler units (110, 120, 130), calculates the power spectral density (PSD) of each Doppler signal, calculates one parameter, the maximum flow velocity, or "envelope", and passes all this data to the Host computer.

The second DSP section 300 receives the PSD of the first Doppler unit 110 and the envelope from the Host computer. The second DSP then determines the presence or absence of an embolus based on a history of PSD 1 and the envelope function.

The Host computer 400 manages changes initiated by the user at the keyboard 450 in various run time parameters. The Host computer writes PSD data to the video display 440 immediately after it is received from the first DSP 200. This data is displayed optionally as a power spectrum or an amplitude spectrum. The Host computer 400 also writes various real-time parameters such as power levels for each Doppler unit, gate depth, etc., to the video display for monitoring by the user. The Host computer 400 stores digitized Doppler shift data to a RAM buffer 420. When an embolus is detected by DSP2 300, the Host computer 400 is signalled and the RAM buffer 420 is written to hard disk 430. Finally, the Host computer 400 calculates parameters that characterize emboli as either formed element or bubble, and determines an approximate size for each embolus that is formed element.

Doppler Units Of FIG. 1

Each pulse Doppler unit (110, 120, 130) operates at a unique center frequency. In the preferred embodiment, the three Doppler units 110, 120, 130 operate respectively at 2.0 Mhz, 1.714 MHz, and 1.2 MHz, although other or identical frequencies may be selected. The transmit bursts from each Doppler unit must be coherent, thus these frequencies may be achieved by integer divides from a master clock. For example, the three frequencies used here can be obtained from a 48 MHz master clock, by dividing the clock by 6, 7, and 10 to respectively obtain four-phase clocks for Doppler units 1, 2 and 3. The three frequencies are chosen to enable sizing and characterization of emboli, and as such they should be well-separated from each other to interrogate an embolus over varying frequency.

Figure 2:
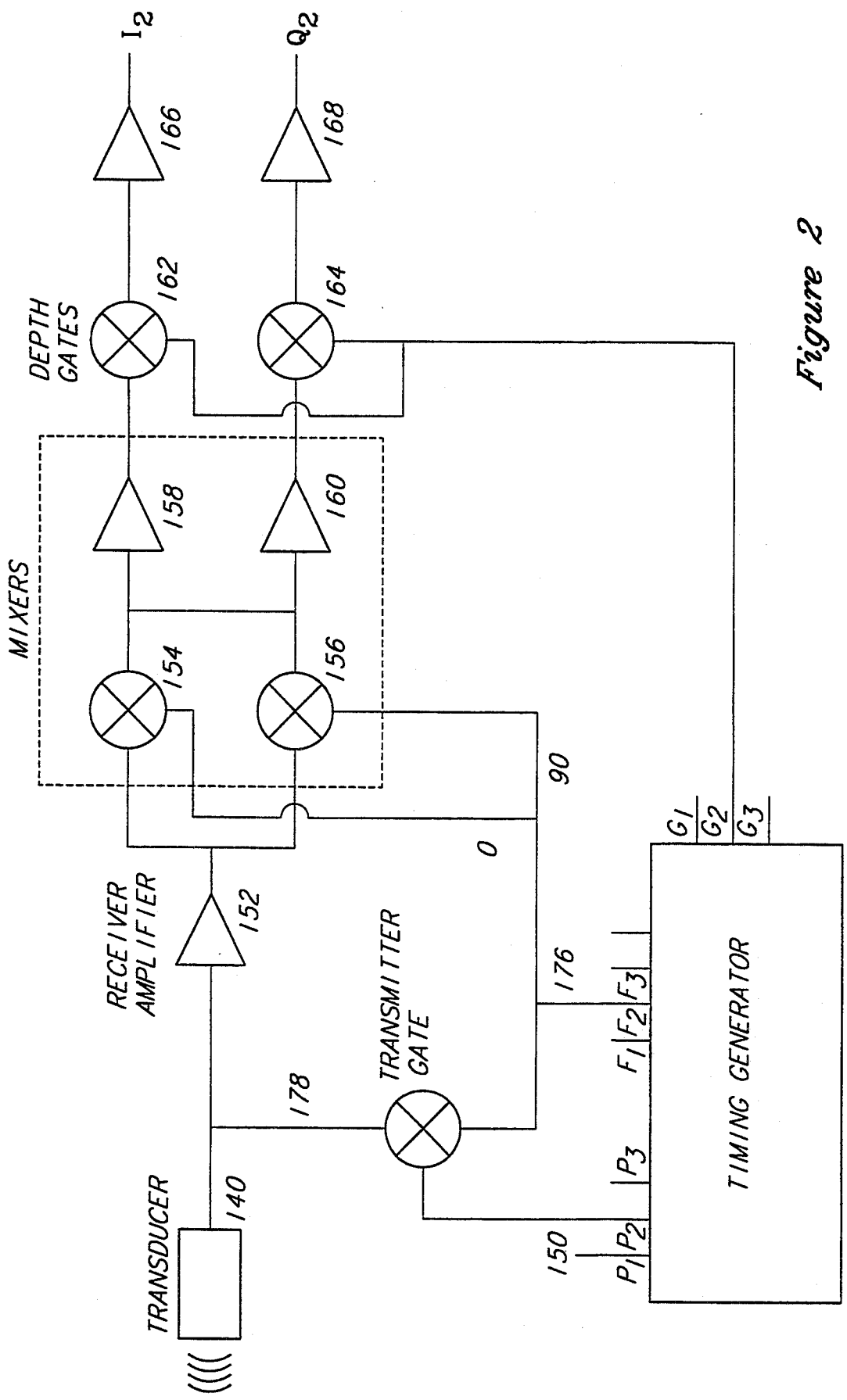
FIG. 2 is an electrical schematic of a pulse Doppler unit used in the embodiment of FIG. 1.
Figure 3A:
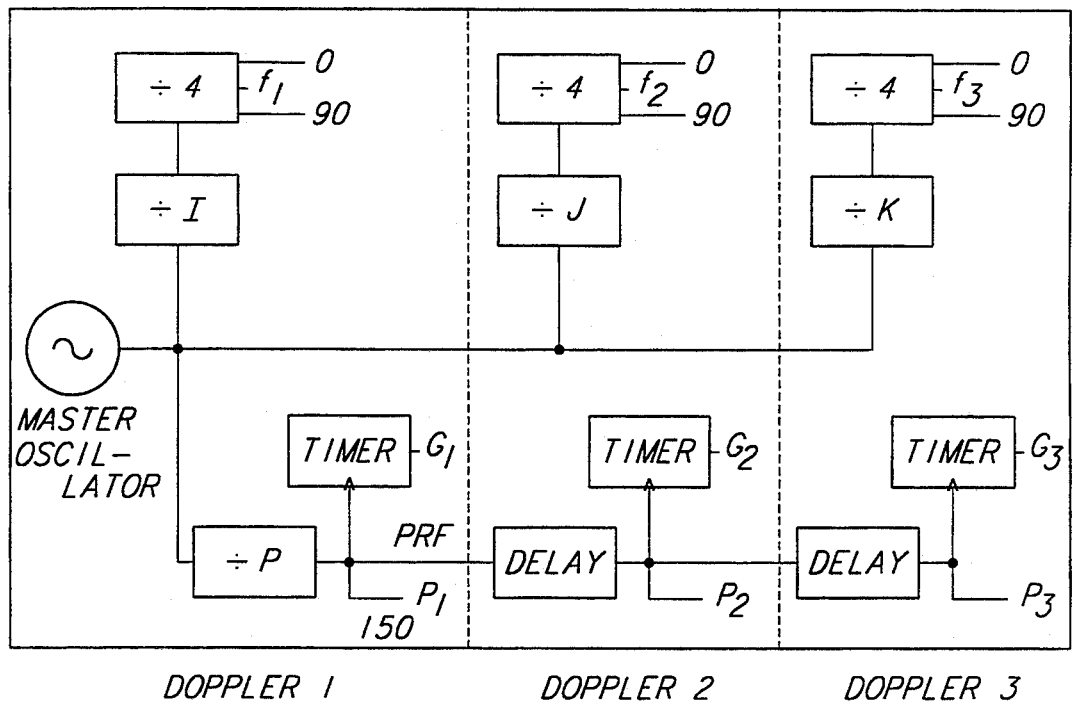
FIG. 3 is a schematic and timing diagram an electrical schematic of the circuitry used to generate the timing pulses for the pulse Doppler unit shown in FIGS. 1 and 2.
Figure 3B:
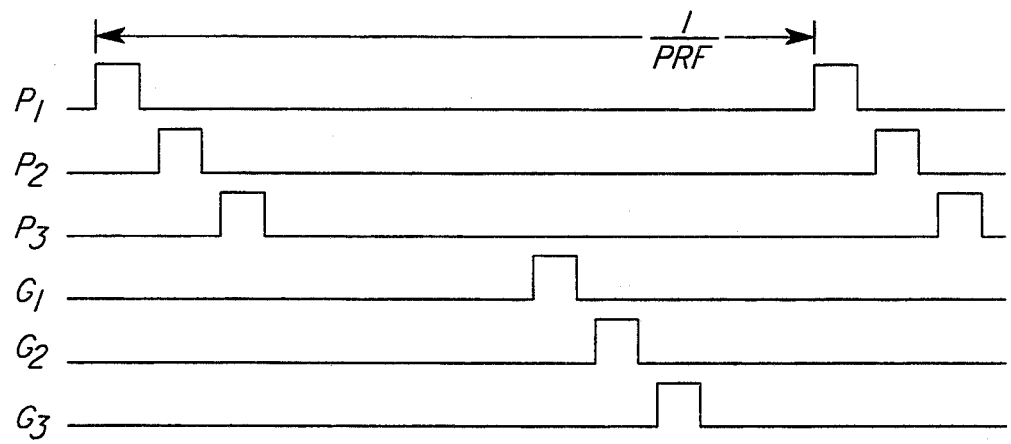

The schematic for each Doppler unit (110, 120, 130) is illustrated in FIG. 2. The circuitry shown schematically in FIG. 2 is replicated for each carrier frequency. A continuous oscillator operating at the carrier frequency 176 is gated coherently to generate a tone burst comprised of multiple cycles of the carrier frequency. The rate of gating of the transmitter is known as the pulse repetition frequency (PRF) which effectively is the sampling rate at which the ultrasound is transmitted into the body. The pulse repetition frequency is obtained from the same master clock that generates the carrier frequencies for each Doppler unit (this is required for coherent transmit bursts from each Doppler unit). Each Doppler unit runs at the same pulse repetition frequency, and the transmit bursts from all three Doppler units may be staggered in time so that they do not overlap. This is accomplished by using a common trigger 150 that fires at the desired pulse repetition frequency, but with the appropriate delay for each Doppler unit. The clocking 150 for this common trigger, as well as for carrier frequency generation, is further described by FIG. 3. The receiver depth gates are also appropriately delayed so that each Doppler unit observes the same sample volume. Note in FIG. 3 that by gating two timers with P1, two range gates are obtained, each at different sites in the same vessel. This is permitted because the depth gate (as well as the carrier frequency) for each Doppler unit is independently adjustable and coherent with the other Doppler units.

A transducer 140 is used to both transmit the tone bursts into the body and receive echoes from within the body. All Doppler units preferably but not necessarily connect to this same transducer 140. This transducer converts electrical signals to ultrasonic signals that reflect off the blood flow being interrogated. These echoes are amplified and bandpassed 152 to eliminate the signals from the other Doppler units, and passed on to a pair of mixers (154, 156), i.e., the receiver amplifier 152 for each Doppler unit is tuned to accept the signals only in the narrow band around the frequency of interest for that Doppler unit. It is also a requirement that the transducer 140 has sufficiently broad bandwidth to provide sufficient sensitivity at all carrier frequencies.

These mixers, after low pass filtering (158, 160), generate the two signals corresponding to the in phase and quadrature signals. The depth of axial sampling within the body is selected by gating (162, 164) the I and Q signals simultaneously with a pulse which is time delayed from each transmit pulse 178 where the delay in time (T) corresponds to a depth in the body x, where x=CT/2, with C equal to the speed of sound in the body. The output from these depth gates corresponds to the complex Doppler audio signal, the frequency of which is proportional to the velocity of moving targets at the depth selected and the amplitude which is proportional to the scattered power from the moving targets in the sample volume. These signals are amplified (166, 168) prior to digitization (front end of section 200).

For detection of emboli, the most important feature of the Doppler electronics is that the mixers (154, 156) must have sufficient dynamic range such that the relatively large amplitude signals produced by a passing embolus are not distorted. This is necessary because the characterization algorithms are based upon linear signal theory.

First Digital Signal Processor (DSP) 200 Of FIG. 1

The first digital signal processor 200 shown in FIG. 1 is immediately downstream of the Doppler section 100. The front end of DSP 200 consists of a multiplexer 210 and a 12 bit A/D 220. The multiplexer 210 allows the complex quadrature signals from more than one Doppler unit (110, 120, 130) to be organized into one input stream, which is then digitized 220. The A/D converted data is written to a FIFO 230, and a counter 240 is decremented with every write. When the counter equals 0, an interrupt generator 250, such as a one-shot, is triggered thereby causing the data in the FIFO 230 to be transferred to a RAM 270 and processed by a conventional CPU 260. The counter 240 is reloaded with a variable NPTS designating the number of A/D conversion clock cycles between hardware interrupts, and digitization continues, such that there is no gap created in the data stream entering the FIFO 230. Results of the processing of this new batch of data are written to the output BIFO (bi-directional FIFO) 280, for further processing by the Host computer 400 and DSP2 300. The Host computer 400 can communicate commands to or from either DSP (200, 300) via 16 bit bidirectional ports through respective buffers 290 and 340.

Figure 4:
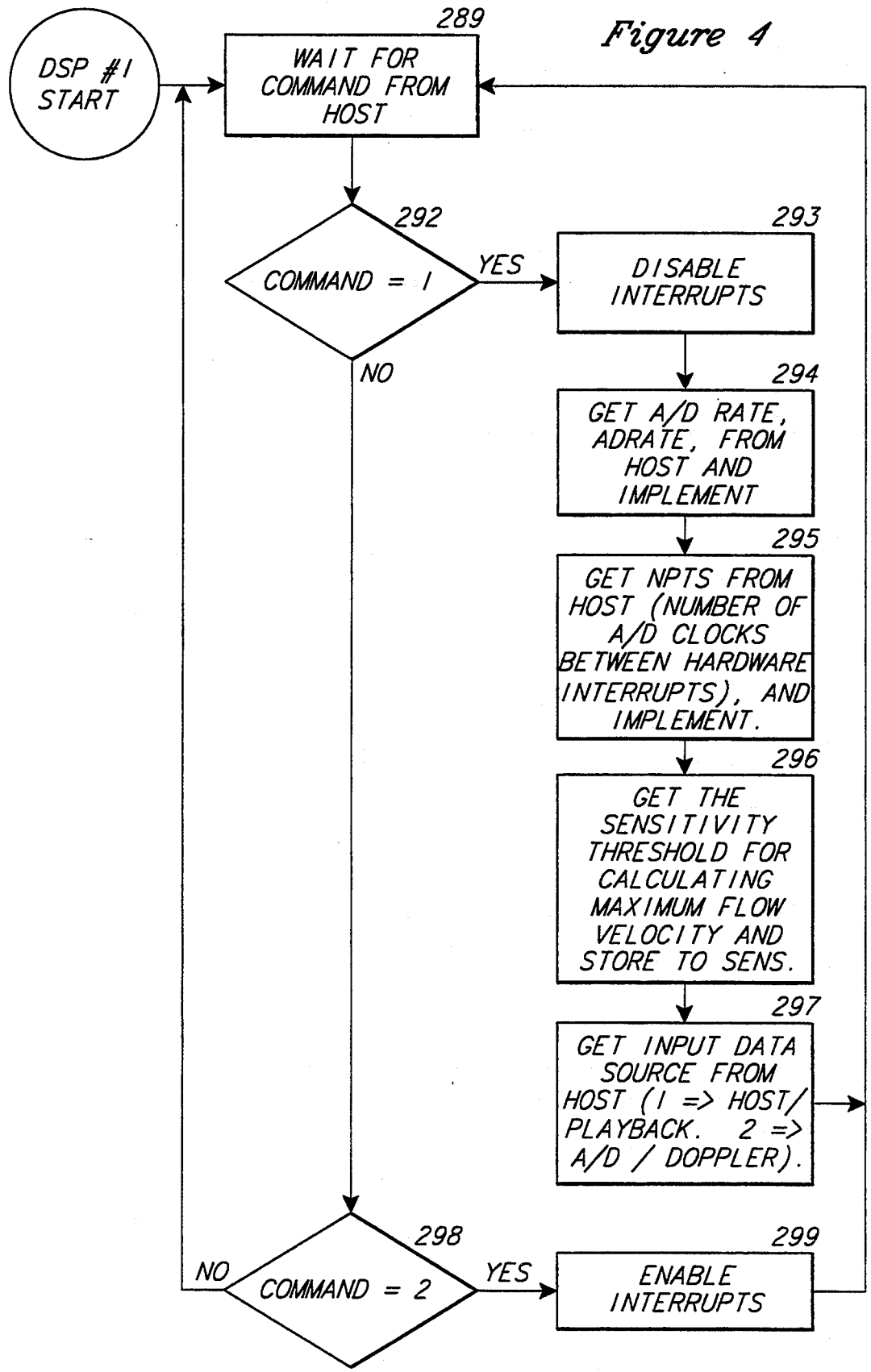
FIG. 4 is a flow chart of the software controlling a first digital signal processor used in the embodiment of FIG. 1.
Figure 5A:
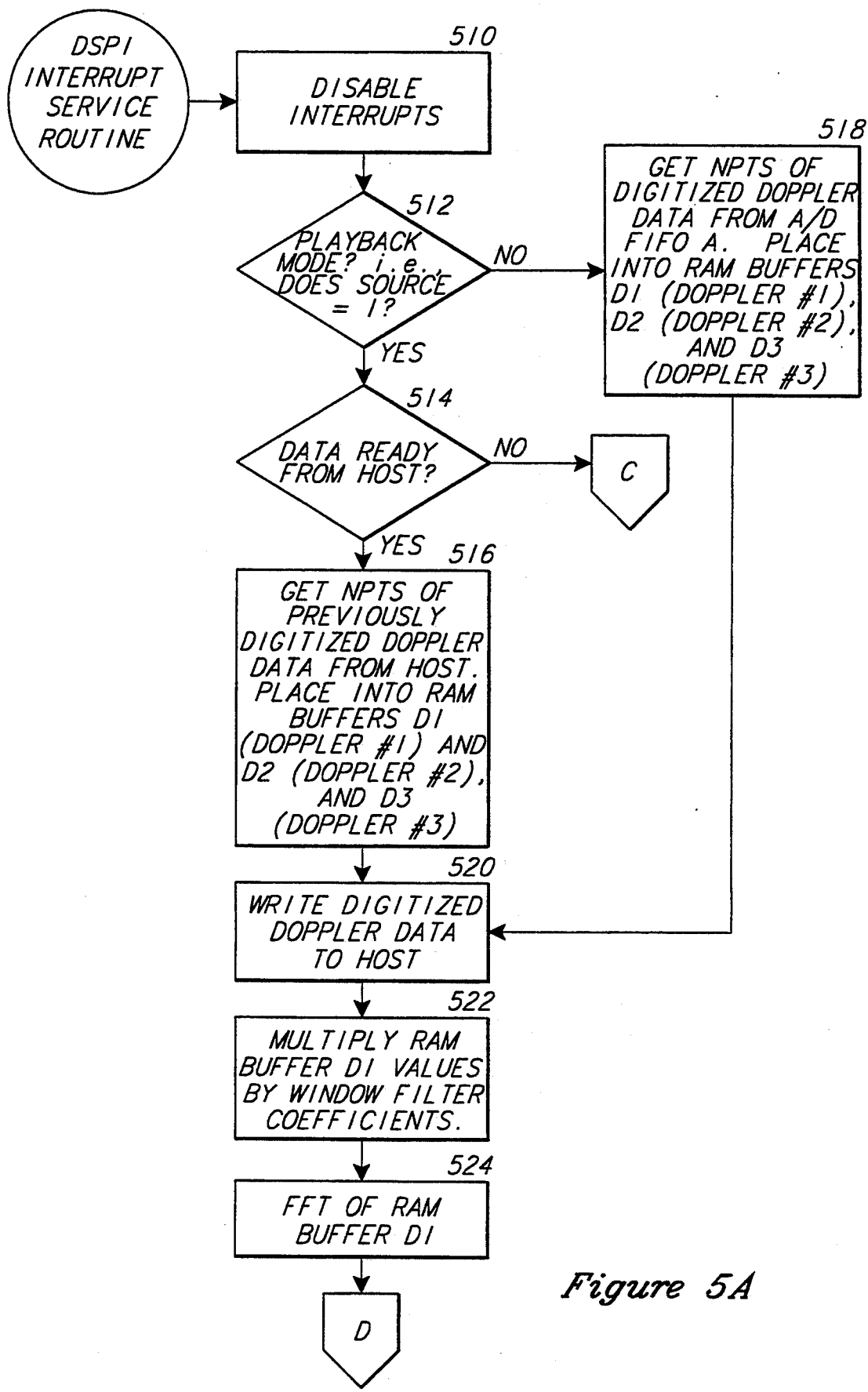
FIG. 5 is a flow chart of a subroutine for servicing interrupts in the first digital signal processor used in the embodiment of FIG. 1.
Figure 5B:
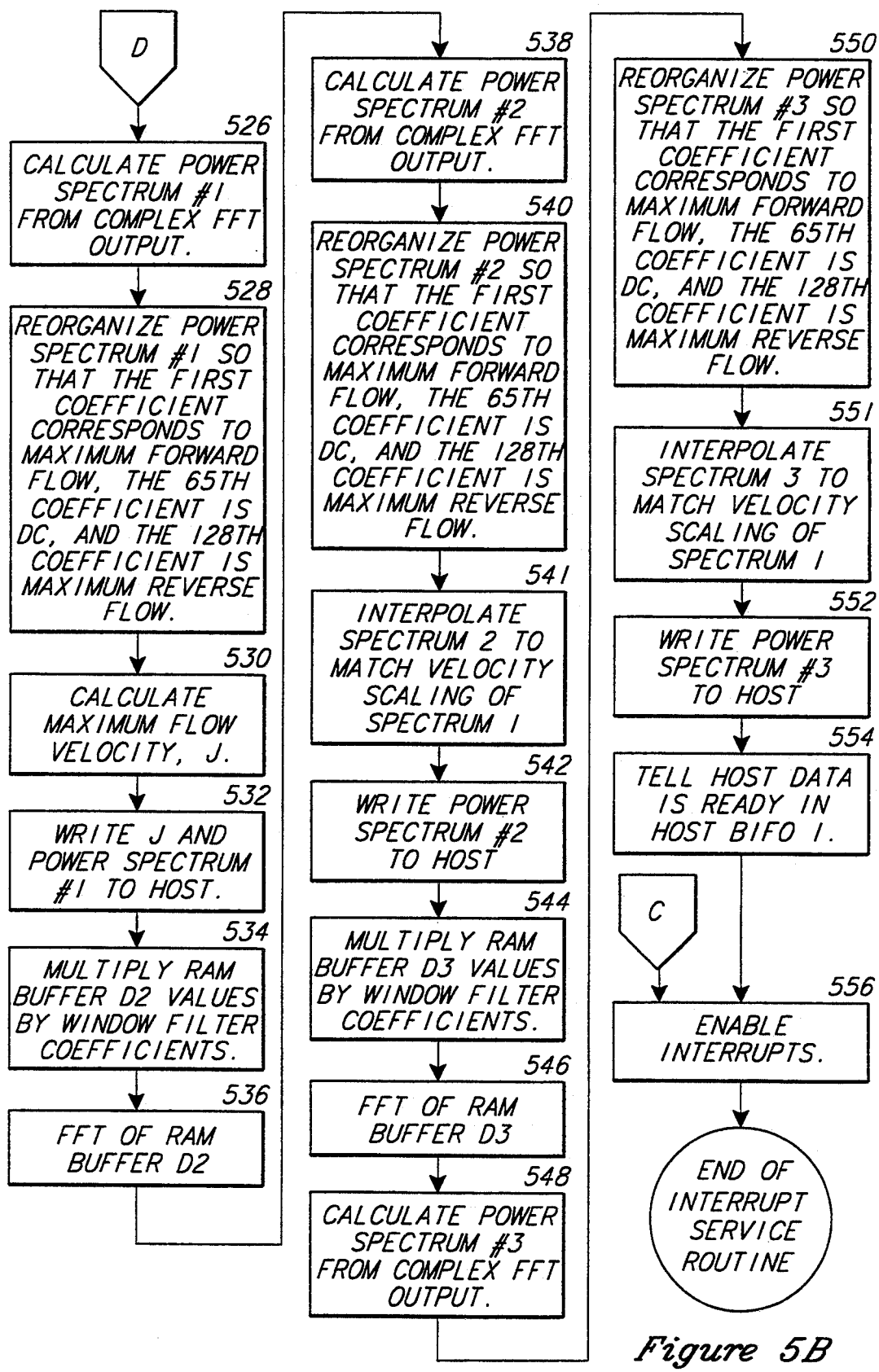
Figure 6:
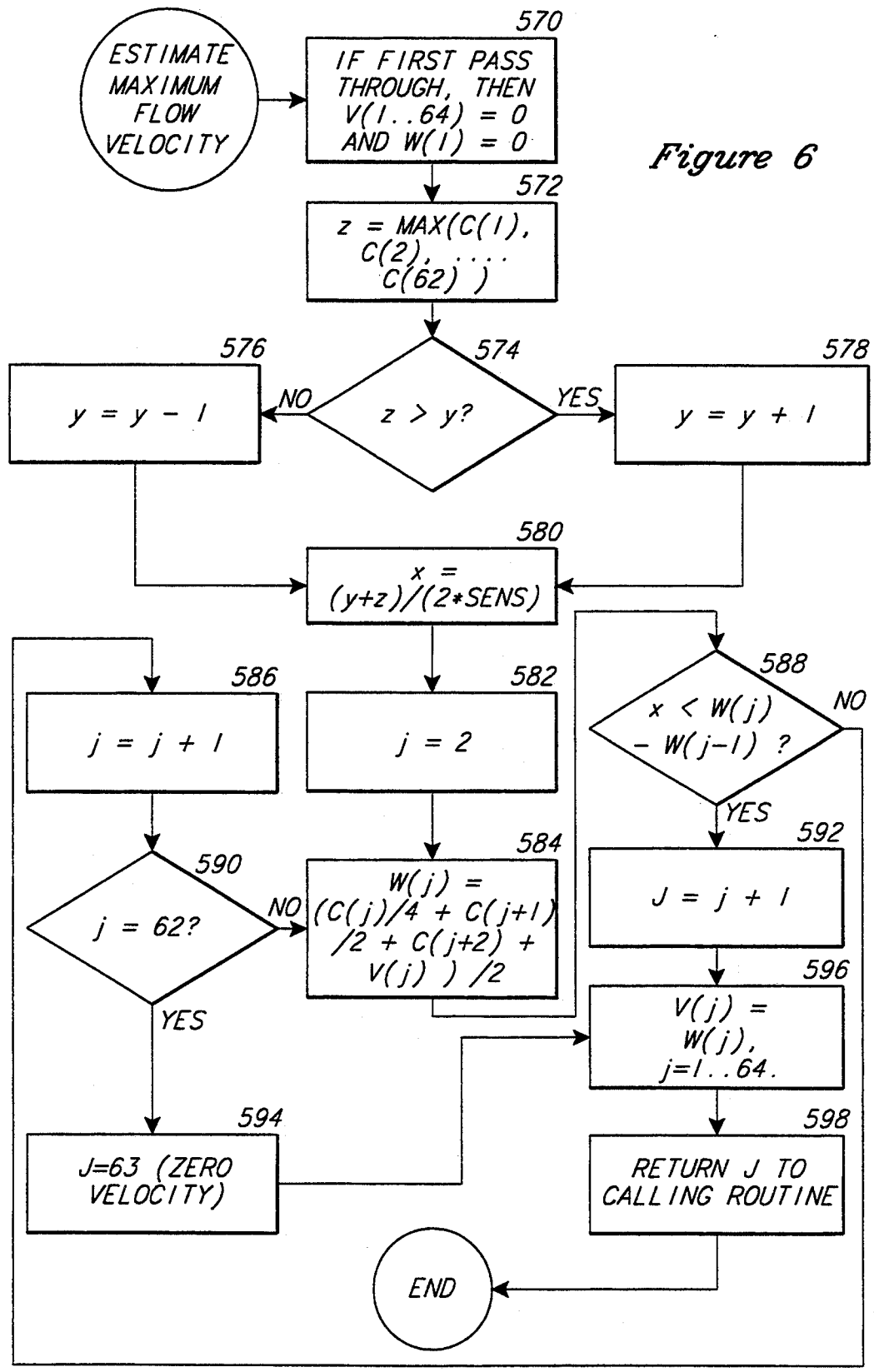
FIG. 6 is a flow chart of a subroutine for calculating the maximum flow velocity used in the interrupt service subroutine of FIG. 5.

The software controlling the first DSP 200 is described in FIGS. 4, 5, and 6. FIG. 4 is the high-level software that allows modification of several operating parameters, and enables interrupts so that the interrupt service subroutine of FIG. 5 becomes active. The interrupt service subroutine illustrated in FIG. 6 processes power spectra from the incoming data. FIG. 6 details the subroutine for calculating the maximum flow velocity at a particular point in time.

High-Level Software Of FIG. 4 For Controlling Second DSP

The high-level software of FIG. 4 runs without termination once it is activated. The purpose of this software is to act as an executive and carry out either of two commands from the Host computer 400. The software begins by waiting at 289 for a command from the Host computer 400 via buffer 290. A command of "1" detected at 292 indicates that the interrupt service subroutine is to be disabled at 293. If so, operational parameters are to loaded at steps 294, 295, 296, and 297. A command of "2" detected at step 289 indicates that the interrupt service subroutine of FIG. 5 is to be activated by enabling interrupts at 299.

In FIG. 4, the parameters loaded under a "1" command are ADRATE (the A/D conversion rate) loaded at 294, NPTS (the number of A/D conversion clock cycles between hardware interrupts) loaded at 295, SENS (the sensitivity threshold for calculating the maximum flow velocity) loaded at 296, and SOURCE (indicates whether data comes from files stored on hard disk 430 in the Host computer 400, or the Doppler units 100 via the A/D 220) loaded at 297. ADRATE is loaded by writing this value to a counter that controls the A/D circuitry 224 at step 294. NPTS 295 is loaded by writing this value to down-counter 240 that controls the hardware interrupt generator 250 at step 295. SENS 296 and SOURCE 297 are loaded by storing these values to RAM 270 at steps 296, 297, respectively, for access by software described below which is also stored in RAM 270.

DSP1 Interrupt Service Subroutine Of FIG. 5

The DSP1 interrupt service subroutine (ISS) 500 called at 299 if a "2" command is detected at 299 (FIG. 4) is illustrated in FIG. 5. The tasks of this subroutine are: (1) to bring in digitized Doppler shift data from the A/D 220 or from the Host computer 400, (2) to calculate the power spectral densities corresponding to each of the three Doppler units (110, 120, 130), (3) to determine the maximum flow velocity from Doppler unit 1 110, and (4) to communicate the Doppler shift data, the PSDs and the maximum flow velocity to the Host computer 400.

The ISS begins by disabling interrupts at 510 so that nested interrupts are disallowed i.e., the ISS is not to be re-activated while it is in the process of handling an interrupt). The ISS examines the value of SOURCE at step 512 to determine whether the incoming data is from the A/D (real-time acquisition) or from the Host computer 400 (Playback mode). If the data is to come from the Host computer 400, then the ISS determines at step 514 if a flag has been written into buffer 290 from the Host computer 400, indicating that NPTS of data are ready in BIFO 1 280 (FIG. 1). If the data is to come from the Host computer 400 and no data is found at 514 to be present in BIFO 1 280, then the ISS enables interrupts at 556 and returns control to the main program (FIG. 4).

If data is ready for processing ("YES" at 514 or "NO" at 512), the ISS reads it from the appropriate FIFO at either 516 or 518. The ISS then demultiplexes the data stream and writes it into three RAM 270 buffers: D1, D2 and D3. Each buffer contains Doppler shift signals from one Doppler unit 110, 120, 130. Each buffer is 256 words (128 complex pairs) in length, and the buffers are reorganized such that each word of new data displaces the oldest word in the buffer. The digitized Doppler data is then written to the Host computer 400 via the bidirectional FIFO 1 520.

The power spectrum for each Doppler unit is obtained by processing each buffer, D1, D2 and D3, with the same algorithm. A buffer is first multiplied by a window filter at 522, 534, or 544, in this case a Blackman window. An FFT is then performed at 524, 536, or 546, and a power spectrum is calculated at 526, 538, or 548. Finally, the power spectrum is reorganized at 528, 540, or 550 so that the leading coefficient corresponds to maximum forward flow velocity, and the final coefficient corresponds to maximum reverse flow velocity. This is an arbitrary ordering, but is necessary so that no ambiguity is introduced elsewhere in the various algorithms of this invention. The power spectrum calculation is done "in place", so that the buffers D1, D2 and D3 now contain power spectra rather than Doppler shift signals.

The ISS processing following power spectrum calculation differs at this point 530, 541, or 551 for each buffer. The maximum blood flow velocity for spectrum 1 is calculated by calling a subroutine at 530 that is illustrated in FIG. 6. At step 532 the value calculated at 530 is placed in the RAM 270 variable J and spectrum 1 (buffer D1) is written to the Host BIFO1.

Spectrum 2 (buffer D2) is resampled by interpolation at 541 so that the velocity scaling of spectrum 2 is the same as that for spectrum 1. This difference in scaling arises because a single blood flow velocity will result in different Doppler shifts when different carrier frequencies are used. Spectrum 2 is written to the Host BIFO 1 at step 542.

Finally, spectrum 3 (buffer D3) is resampled by interpolation at step 551 so that the velocity scaling is the same as that for spectrum 1. Spectrum 3 is then written to the Host BIFO 1 at 552. The Host computer 400 is notified at step 554 via buffer 290 (FIG. 1) that data is ready in Host BIFO 1. Interrupts are then enabled at 556, and control returns to the main program (FIG. 4).

Maximum How Velocity Estimating Subroutine Of FIG. 6

The subroutine called at 530 of FIG. 5 for estimating the maximum blood flow (MAXFLOW) velocity is illustrated in FIG. 6. This subroutine is performed to determine the range of velocities that an embolus may assume. If an embolus is detected whose velocity is outside this range, it must be an artifact because an embolus will not travel faster than the surrounding blood. Limiting the range of velocities over which the search for an embolus is performed reduces the computation time required for the embolus detection subroutine. The MAXFLOW subroutine begins by initializing two working arrays, V and W at 570, on the first pass through the subroutine. This step 570 is performed once only. The MAXFLOW subroutine determines the maximum velocity by starting at the highest forward flow velocity coefficient and filtering the spectral coefficients successively towards the DC velocity coefficient. The maximum velocity is located when the change in the output of the filter exceeds a threshold. The threshold, x, is a function of the values y, z, and SENS. z is calculated at 572 by finding the maximum forward flow spectral coefficient. Y is a value that "tracks" z by "delta-modulation," i.e., if the subroutine determines at step 574 that y<z, then y is incremented at 578. If the subroutine determines at step 574 that y>z, then y is decremented at 576. SENS is the user-specified sensitivity threshold for detecting the maximum flow velocity. The threshold x is calculated at 580 as the sum of y and z, divided by twice SENS.

The index for searching through the spectrum for the maximum flow velocity "j" is set to "2" at 582. The filter output, W(j), is calculated at 584 as the weighted average of three adjacent spectral coefficients, C0), C(j+1) and C0+2), as well as a spectral coefficient from the previous spectrum 1, V(j) calculated at 584. In this subroutine, C(j) is synonymous with the spectrum from Doppler unit 1. When W(j)−W(j−1) is found to exceed x at step 588, the index "j" is incremented by one at step 592. Note this is the index within Spectrum 1 corresponding to the maximum flow velocity. If W(j)−W(j−1) is found not to exceed x at 588, then the search index, j, is incremented by one at 586, and the subroutine determines at 590 whether the index "j" has progressed all the way to the DC velocity coefficient 590. If not, the subroutine branches back to step 584 where the search continues. If the subroutine determines at step 590 that the search has gone all the way to DC, then zero velocity is specified by setting the index "j" to the DC index at step 594. The MAXFLOW subroutine ends by returning the index "j" to the calling routine at 598.

Figure 7:
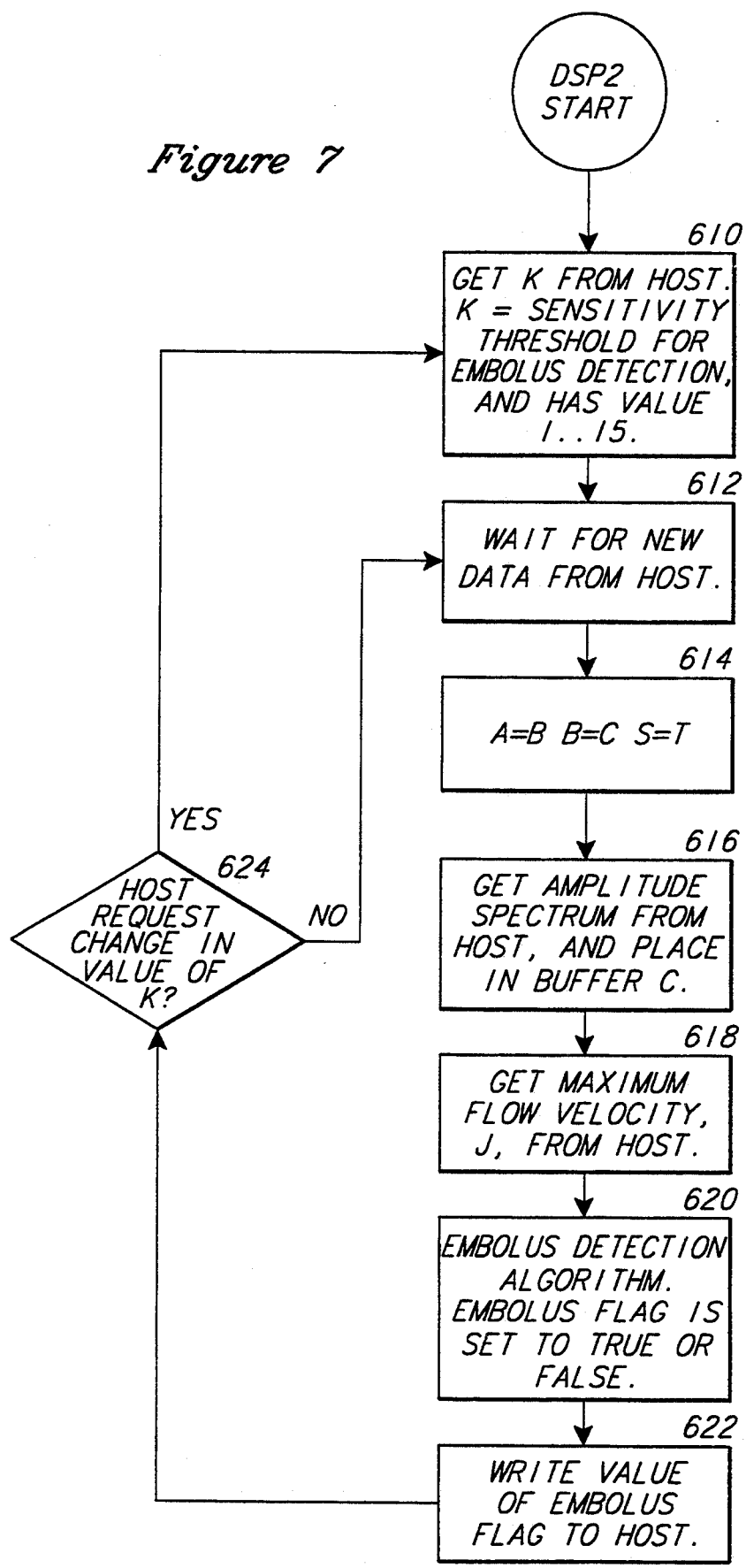
FIG. 7 is a flow chart of the software controlling a second digital signal processor used in the embodiment of FIG. 1.

Second Digital Signal Processor Software Of FIG. 7

With reference to FIG. 1, the second digital signal processor DSP 300 has the sole responsibility to detect emboli and indicate their presence to the Host computer 400. The detection is done on spectrum 1 and the value J, which correspond to the amplitude spectral density from Doppler unit 1, and the maximum flow velocity calculated in the MAXFLOW subroutine explained above with reference to FIG. 6. The second DSP is similar in architecture to the first DSP 200 in that it has the same CPU 320, RAM 330, Host BIFO 310, and buffer 340. These components of the second DSP 300 are laid out in the same configuration as those in the first DSP 200, and for purposes here are indexed by 2 instead of 1 (e.g., DSP2, RAM 2, Host BIFO 2, etc.).

Figure 8A:
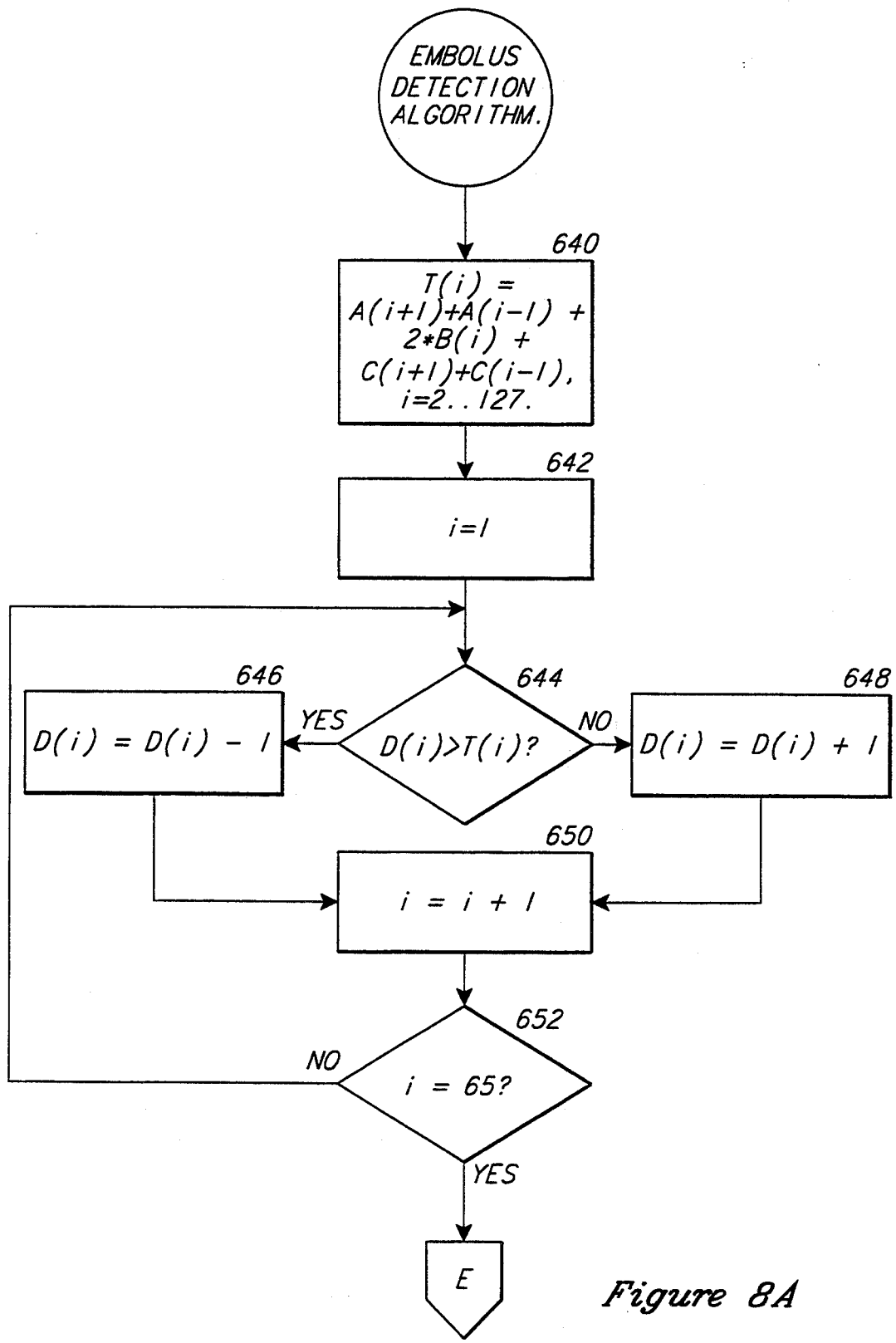
FIG. 8 is a How chart of an embolus detection subroutine used in the digital signal processing software of FIG. 7.
Figure 8B:
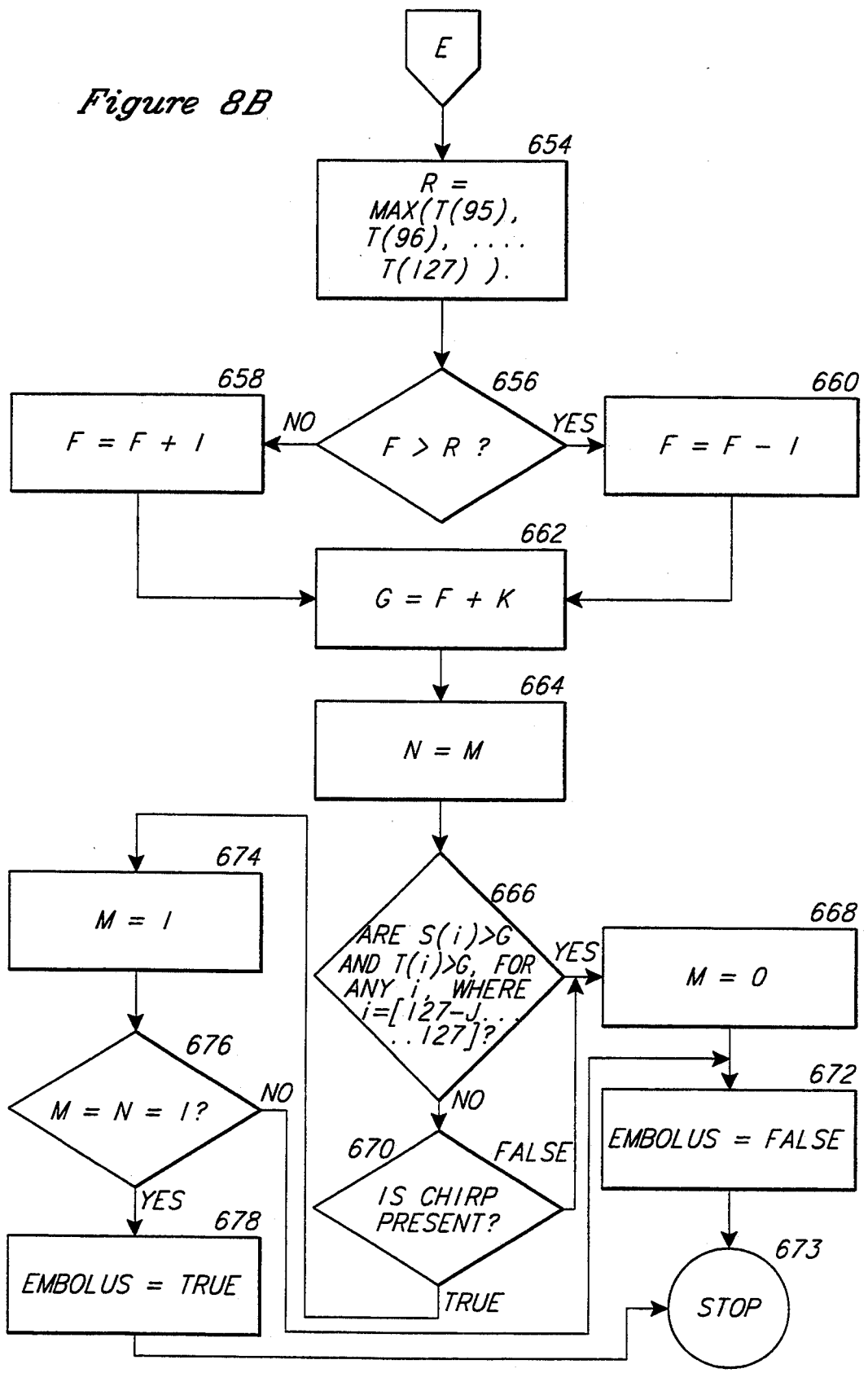
Figure 9A:
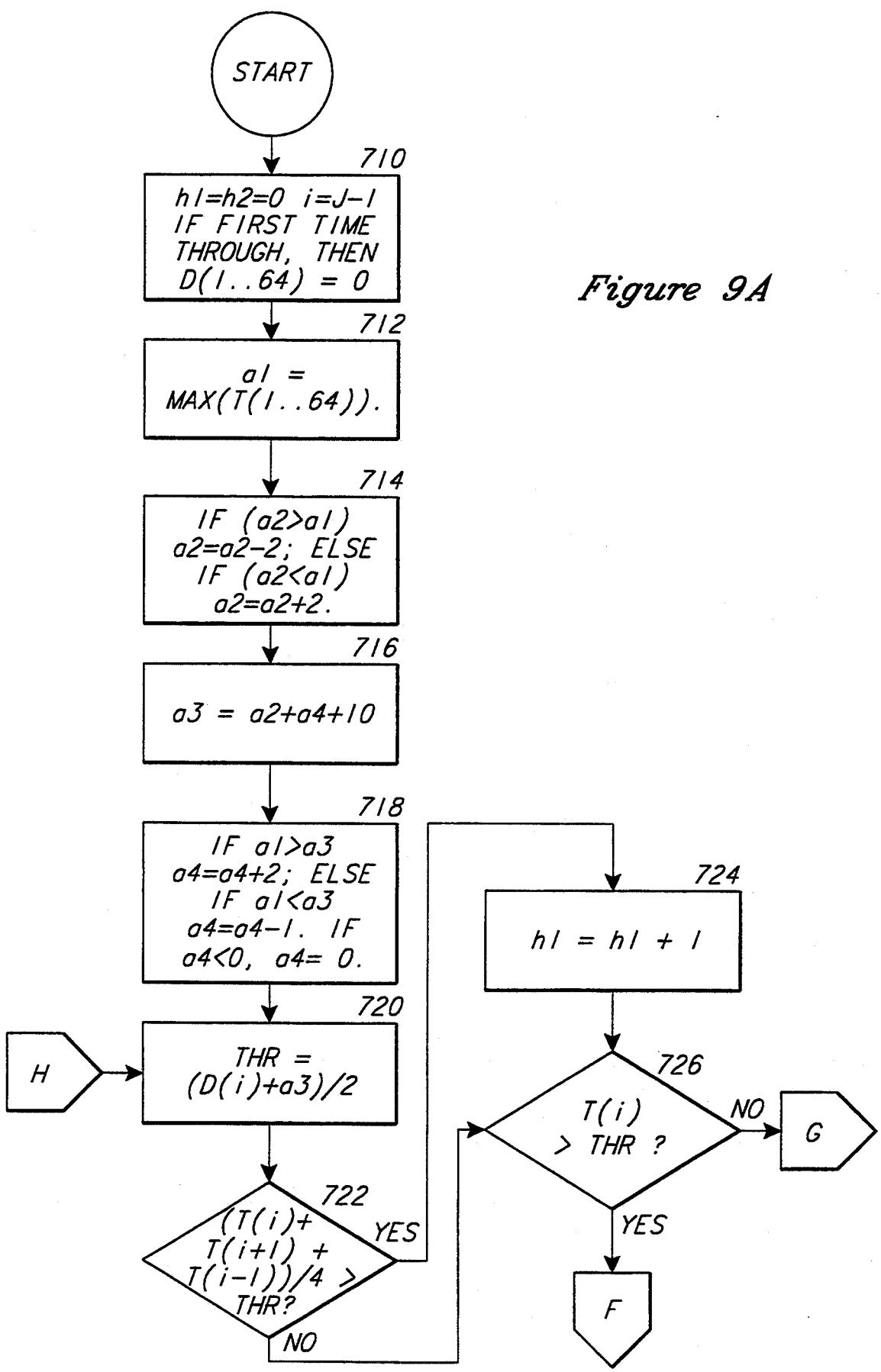
FIG. 9 is a flow chart of a "chirp" detection subroutine used in the embolus detection subroutine of FIG. 8.
Figure 9B:
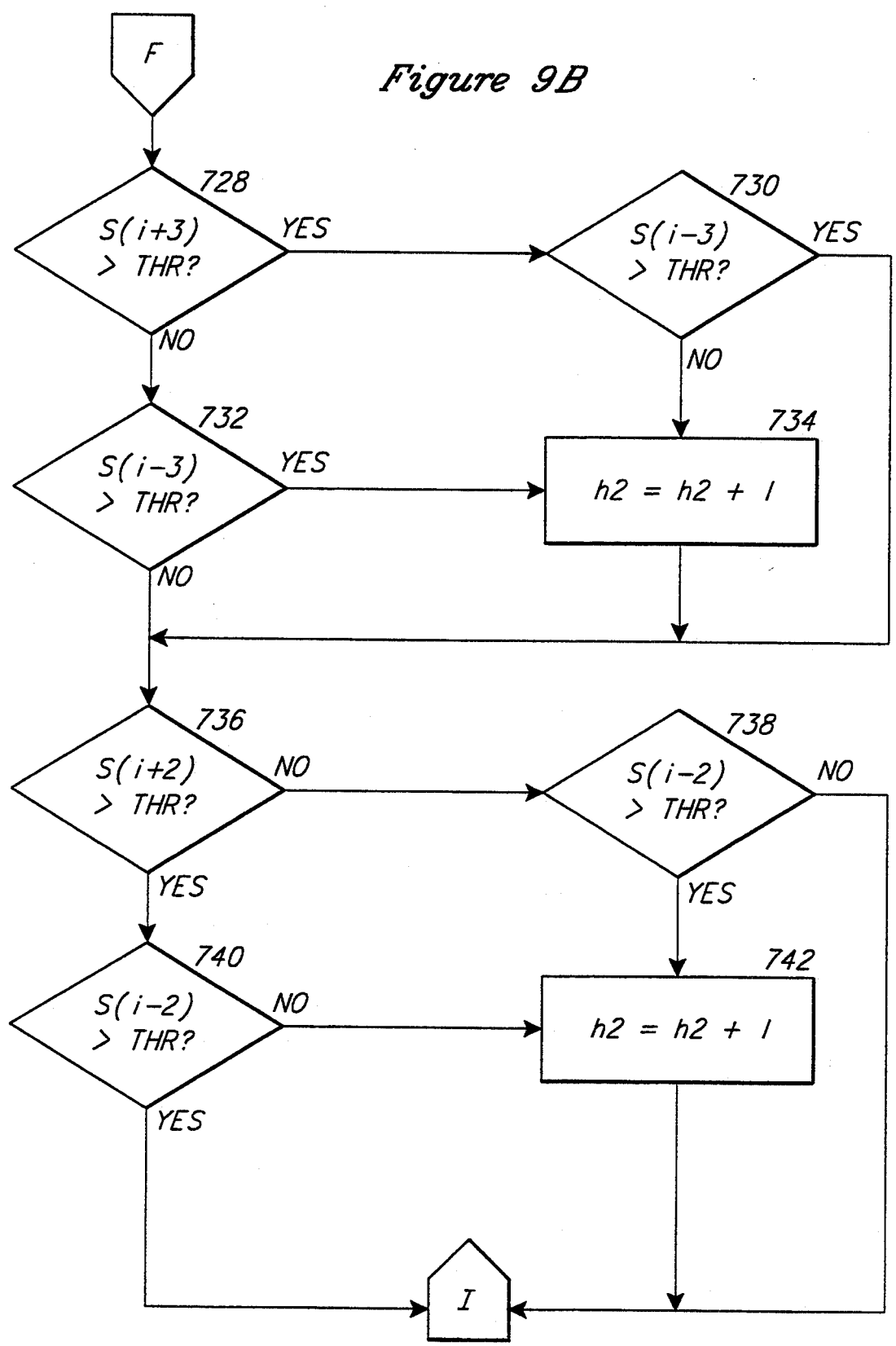
Figure 9C:
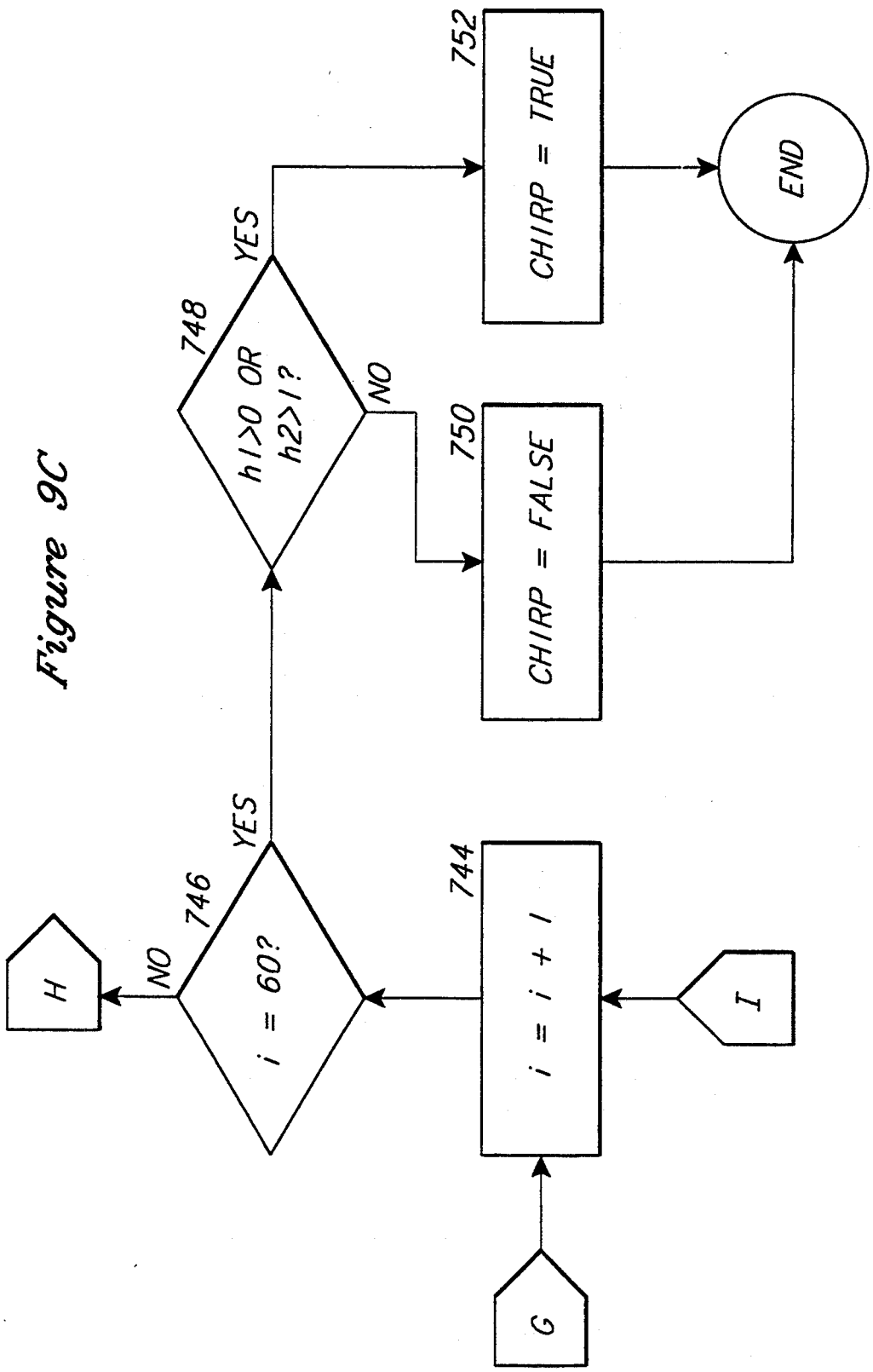

The software controlling the second DSP 300 is described in FIGS. 7, 8, and 9. FIG. 7 is a flow chart of the high-level software. This subroutine obtains data from the Host computer 400 and invokes an embolus detection subroutine shown in FIG. 8. FIG. 9 is a flow chart of one component of the embolus detection subroutine, also known as the "chirp" detector. Some global variables that are used at all levels of FIGS. 7, 8, and 9 are amplitude spectra "A, .... B" and "C," and filtered amplitude spectra "S" and "T", "C" is the most recent amplitude spectrum originating from Doppler unit 1. "B" is the previous value of "C" and "A" is the previous value of "B." "T" is a weighted average of "A, ... . B" and "C," and "S" is the previous value of "T" when a single Doppler channel is being utilized to detect emboli. Alternatively, "S" may be a weighted average of spectra from a second channel of the same Doppler unit, as discussed in the description of FIG. 3.

The high-level software shown in FIG. 7 begins by getting the detection sensitivity threshold, K, from the Host computer at step 610. The lower the value of this threshold, the greater the number of false alarms. The user will have control over this value, and may wish to adjust it to accommodate situations of varying SNR, or other clinical monitoring scenarios.

The high-level software of FIG. 7 waits at step 612 for an amplitude spectrum to arrive from the Host computer 400 via Host BIFO 280 (FIG. 1). The arrival is flagged by the Host computer 400 writing value to the buffer 340. When new data are available, the second DSP 300 transfers the current values of arrays "B," "C" and "T" respectively to "A, .... B" and "S" at step 614. It then reads the current values of array "C" and "J" from the Host BIFO 280 at steps 616 and 618, respectively. The second DSP 300 then calls the embolus detection routine at 620 and sets an embolus "flag" to either TRUE or FALSE. The TRUE or FALSE value of this flag is communicated to the host computer 400 at 622. The subroutine then checks buffer 340 at 624 to see if the Host computer 400 wants to change the value "K," and processes any desired changes by returning to step 610. In either event, the DSP2 subroutine returns to wait for more data from the Host computer 400 at 612, thus repeating the DSP2 subroutine of FIG. 7.

Embolus Detection Subroutine Of FIG. 8

The embolus detection subroutine called by the high-level software of FIG. 7 at 620 is illustrated in FIGS. 8 and 9. FIG. 8 lays the groundwork for detecting a chirp, and FIG. 9 is the actual the chirp detection subroutine 670. The four main tasks performed by the subroutine of FIG. 8 are:

Produce a modified spectrum "T" at step 640, from the spectra "A, .... B" and "C." The modified spectrum, "T" is one in which chirp signals are enhanced against the background blood flow. T(i) is calculated at step 640 using the formula $A(i+1)+A(i-1)+2*B(i)+C(i+1)+C(i-1)$, where i runs from 2 to 127.

Update an array of thresholds, D(0 . . . 64) at steps 642–652 for separating the embolic signals from signals due to background blood flow. The Doppler shift signal power due to blood flow often varies with velocity, and thus each threshold applies to a particular forward flow velocity. The thresholds, D(1..64), follow their respective spectrum coefficients, T(1..64), through delta-modulation, i.e., the index i is set to "1" at step 642. At each value of i, if D(i) is found to be less than T(i) at step 644, then D(i) is incremented by one at 648. If D(i) is found to be greater than T(i) at step 644, then D(i) is decremented by one at 646. "I" is then incremented by one at 650. Finally, a determination is made at 652 to determine whether the final value of "i" has been reached. If so, the subroutine advances to step 654. Otherwise, the subroutine returns to step 644 to modify D(i) according to the next value of "i". In this manner, D(i) is repetitively modified at steps 644–648 until "i" is found to equal 65 at step 652.

Determine if reverse flow artifact is present (usually due to saturation of Doppler unit 1 110 or the associated digitized Doppler shift signals). The first step to determine if such artifact is present is to calculate the maximum amplitude of a set of reverse flow coefficients, R at step 654. The value of "R" is tracked by "F," through delta-modulation, i.e., if the subroutine determines at step 656 that "F"<"R" then "F" is incremented by one at 658. if the subroutine determines at step 656 that "F">"R" then "F" is decremented by one at 660. The user-specified detection sensitivity, "K," is added to "F" at 662 to set a threshold "G" for artifact detection. In preparation for the search for reverse flow artifact, the value of "M" is saved as "N" at step 664. "N" indicates if a chirp was detected in the previous pass through the subroutine. The search for artifact is performed over a velocity range from the negative of the maximum flow velocity (FIG. 6), to the maximum reverse flow velocity detectable. The spectral indices for this search are [127-J . . . 127]. The embolus detection subroutine checks at 666 to determine if S(i)>"G" and T(i)>"G" for any index i in this range of spectral indices. If so, then artifact is assumed and the value "M" is set to 0 at step 668 to indicate that an embolus has not been detected. The flag EMBOLUS is also set FALSE at step 672, and the subroutine then stops at step 673. If the embolus detection subroutine determines at step 666 that either S(i)<"G" or T(i)<"G" for any index i, the chirp detection subroutine is called at 670. The chirp detection subroutine is explained below with reference to FIG. 9.

Process the results of the chirp detection subroutine. If the chirp detection subroutine determines that an embolus is present, it sets the value "M" equal to 1, at step 674. Otherwise, the subroutine branches to 668 where the value "M" is set to 0 as described above. If the subroutine branched to 674 to set "M" equal to 1, it then checks at step 676 to determine if both values "M" and "N" are equal to i.e. the present value of "M" and the prior value of "M" are both the same. If both values are not the same, then an embolus is assumed not to be present, and the subroutine branches from 676 to step 672 to set the EMBOLUS flag FALSE as described above. If the subroutine determines at 676 that the value "M" is not equal to the value "N," then the EMBOLUS flag is set TRUE at step 678, and the subroutine stops at step 673 as described above.

Chirp Detection Subroutine Of FIG. 9

The chirp detection subroutine called by the embolus detection subroutine at 670 is illustrated in FIG. 9. This subroutine examines two adjacent spectra and looks for a narrow band "chirp" that is indicative of an embolus passing through the sample volume. This chirp is evidenced by a high amplitude, narrow band signal that typically changes pitch between adjacent spectra in arteries such as the mid-cerebral artery, but may remain a constant tone in vessels such as the pulmonary artery. The adjacent spectra are the value of "T" calculated at step 640 (FIG. 8) and "S" calculated at step 614 of FIG. 7.

The chirp detection subroutine begins at 710 by initializing the chirp counters h1 and h2 and setting the index i to just below the maximum forward velocity, J-1. If the subroutine is being called for the first time, the detection thresholds D(1.64) are also set to zero at 710.

Four thresholds are then calculated prior to searching for a chirp: a1, a2, a3 and a4. a1 is set to the maximum forward flow coefficient of "T" at 712. The threshold a2 is then set at step 714 using delta-modulation. Thus, if a2>a1, then a2 is decremented by 2. If a2<a1, then a2 is incremented by 2. The threshold a3 is calculated at 716 as the sum of a2, a4 and 10. The threshold a4 is then modified at step 718. If a1>a3, then a4 is incremented by 2. Otherwise, a4 is decremented by 1. If a4 becomes less than zero, then a4 is set to zero.

As mentioned above, the index i is set at 710 to just below the maximum forward flow velocity, i.e., J-1. At this initial and each subsequent value of i, a threshold THR is calculated at step 720 as the average of D(i) and a3.

In this embodiment for detection of emboli in the carotid or cerebral circulation, three types of chirps are tested for: (1) a "vertical chirp" which is a very quick change in frequency indicative of an embolus that passes through the sample volume so quickly that it is present in only a single spectrum taken at one point in time, (2) an "ascending chirp" which is an increasing frequency representing an embolus that is accelerating but passing through the sample volume sufficiently slowly that it is present in several spectra taken at different points in time, and (3) a "descending chirp" which is a decreasing frequency representing an embolus that is decelerating but passing through the sample volume sufficiently slowly that it is present in several spectra taken at different points in time. Ascending and descending chirps can further be classified as "steep" or "shallow" depending upon how quickly the frequency is increasing or decreasing corresponding to how quickly the velocity of the embolus is increasing or decreasing with respect to time. (If this were the pulmonary artery, a constant tone chirp test would also be used).

The test of chirps type starts at 722 where a weighted average of each of three adjacent coefficients in the current spectrum "T" is compared to the threshold THR calculated at 720. These three adjacent coefficients correspond to three adjacent frequencies representing three adjacent velocity values. A weighted average greater than the threshold THR, is indicative of a vertical chirp. Thus, the subroutine processes from 722 to 724 where hi is incremented by one before progressing to step 726. Otherwise, the subroutine branches from step 722 directly to 726.

The test for ascending and descending chirps begins at step 726 by comparing $T(i)$ with THR. If $T(i) <$ THR, then no further chirp tests are done for this value of i, and i is incremented by one at 744 to examine the next frequency component in the spectrum. It will be recalled that each value of i is indicative of a corresponding frequency component in the spectrum. Thus, if $T(i) <$ THR for a given i, the frequency component corresponding to that i is not very large, thus indicating that the embolus is not moving at the corresponding velocity. The subroutine then determines at 746 if i is equal to 60 (i.e., a frequency component corresponding to near zero velocity). If not, then the testing continues by returning to step 720.

The program executes steps 728–742 to identify which of the chirp types described above is present. The subroutine first checks at 728 to determine whether the $S(i+3)$, i.e., the amplitude of the $i+3$ (third higher) frequency component for the previously obtained frequency spectrum, is greater than the threshold THR. If $S(i+3) >$ THR, subroutine checks at 730 to determine whether $S(i-3) >$ THR. $S(i-3)$ is the amplitude of the $i-3$ (third lower) frequency component for the previously obtained frequency spectrum. If $S(i-3)$ is not greater than the threshold THR, the chirp is considered to be a "steep descending chirp." Thus, a steep descending chirp is indicated by $T(i) >$ THR, $S(i+3) >$ THR, and $S(i-3) <$ THR.

If the subroutine determines at 728 that $S(i+3) <$ THR, the subroutine also checks at 732 to determine whether $S(i-3) >$ THR. If $S(i-3)$ is greater than the threshold THR, the chirp is considered to be a "steep ascending chirp." Thus, a steep ascending chirp is indicated by $T(i) >$ THR, $S(i+3) <$ THR, and $S(i-3) >$ THR.

If the subroutine determines at 730 that the chirp is a steep descending chirp or at 732 that the chirp is a steep ascending chip, a counter h2 is incremented by one at 734. Thus, the counter h2 is incremented each time a steep chirp is detected for a given frequency component i.

The subroutine now progresses to 736 where the test for shallow chirps begins. The subroutine first checks at 736 to determine whether the $S(i+2)$, i.e., the amplitude of the $i+2$ (second higher) frequency component for the previously obtained frequency spectrum, is greater than the threshold THR. If $S(i+2) >$ THR, subroutine checks at 740 to determine whether $S(i-2) >$ THR. $S(i-2)$ is the amplitude of the $i-2$ (second lower) frequency component for the previously obtained frequency spectrum. If $S(i-2)$ is not greater than the threshold THR, the chirp is considered to be a "shallow descending" chirp. Thus, a shallow descending chirp is indicated by $T(i) >$ THR, $S(i+2) >$ THR, and $S(i-2) <$ THR.

If the subroutine determines at 736 that $S(i+2) <$ THR, the subroutine also checks at 738 to determine whether $S(i-2) >$ THR. If $S(i-2)$ is greater than the threshold THR, the chirp is considered to be a "shallow ascending chirp." Thus, a shallow ascending chirp is indicated by $T(i) >$ THR, $S(i+2) <$ THR, and $S(i-2) >$ THR.

If the subroutine determines at 740 that the chirp is a shallow descending chirp or at 738 that the chirp is a shallow ascending chip, then the counter h2 is also incremented by one at 734. Thus, the counter h2 is incremented each time either a steep chirp or a shallow chirp is detected for a given frequency component i. As explained below, if the final value of h2 is greater than a predetermined value corresponding to the detection of a steep chip at a predetermined number of frequency components, an embolus is considered to be passing through the sample volume.

Following these tests, the frequency component index i is incremented at 744, and if it is found at 746 does not exceed 60 (velocity close to zero), then the testing continues by returning to step 720.

When the subroutine determines at 746 that $i=60$, a report is made to the calling routine. If the subroutine determines at 748 that either one or more vertical chirps are detected (i.e., $h1 > 1$, or two or more ascending or descending chirps have been detected (i.e., $h2 > 2$), the CHIRP flag is set TRUE at step 752 to indicate that a chirp has occurred. Otherwise, the CHIRP flag is set FALSE at step 750 to indicate that no chirp has occurred.

Host Computer 400 Of FIG. 1

The host computer 400 shown in FIG. 1 has the sole responsibility of coordinating the activities of all other subsystems 100, 200, 300. It also has the job of presenting information to the user, receiving input from the user, storing digitized data when emboli are detected retrieving digitized data for playback, discriminating between gas and formed element emboli, and sizing formed element emboli. The Host computer 400 consists of conventional components, namely a 25 MHz 386 PC 410, at least 640 kBytes of RAM 420, a hard disk 430, a 640×480 VGA display 440, and a keyboard 450.

Figure 10A:
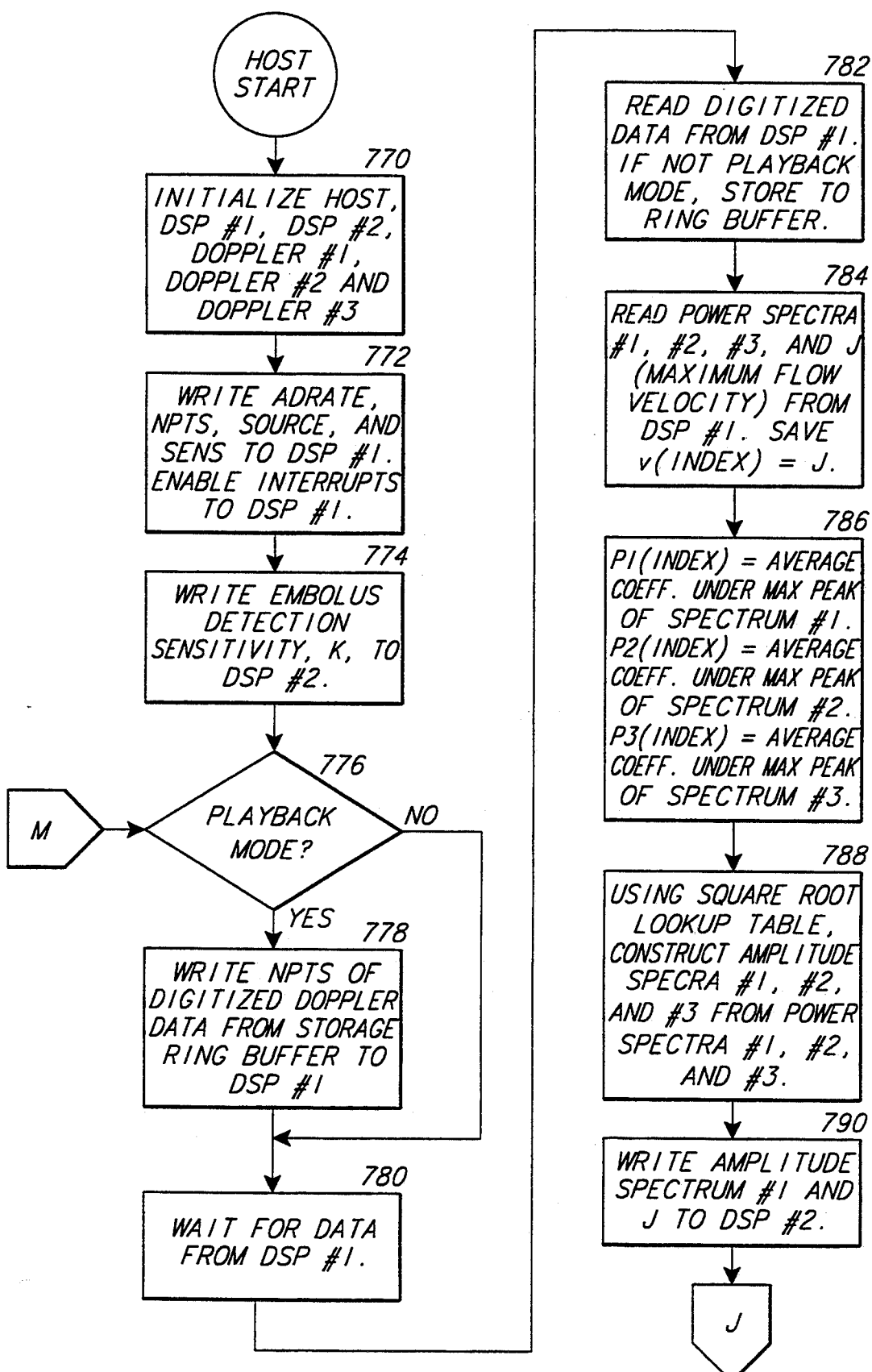
FIG. 10 is a flow chart of software controlling a host computer used in the embodiment of FIG. 1 for controlling coordinating the activity of all other components of the embodiment of FIG. 1.
Figure 10B:
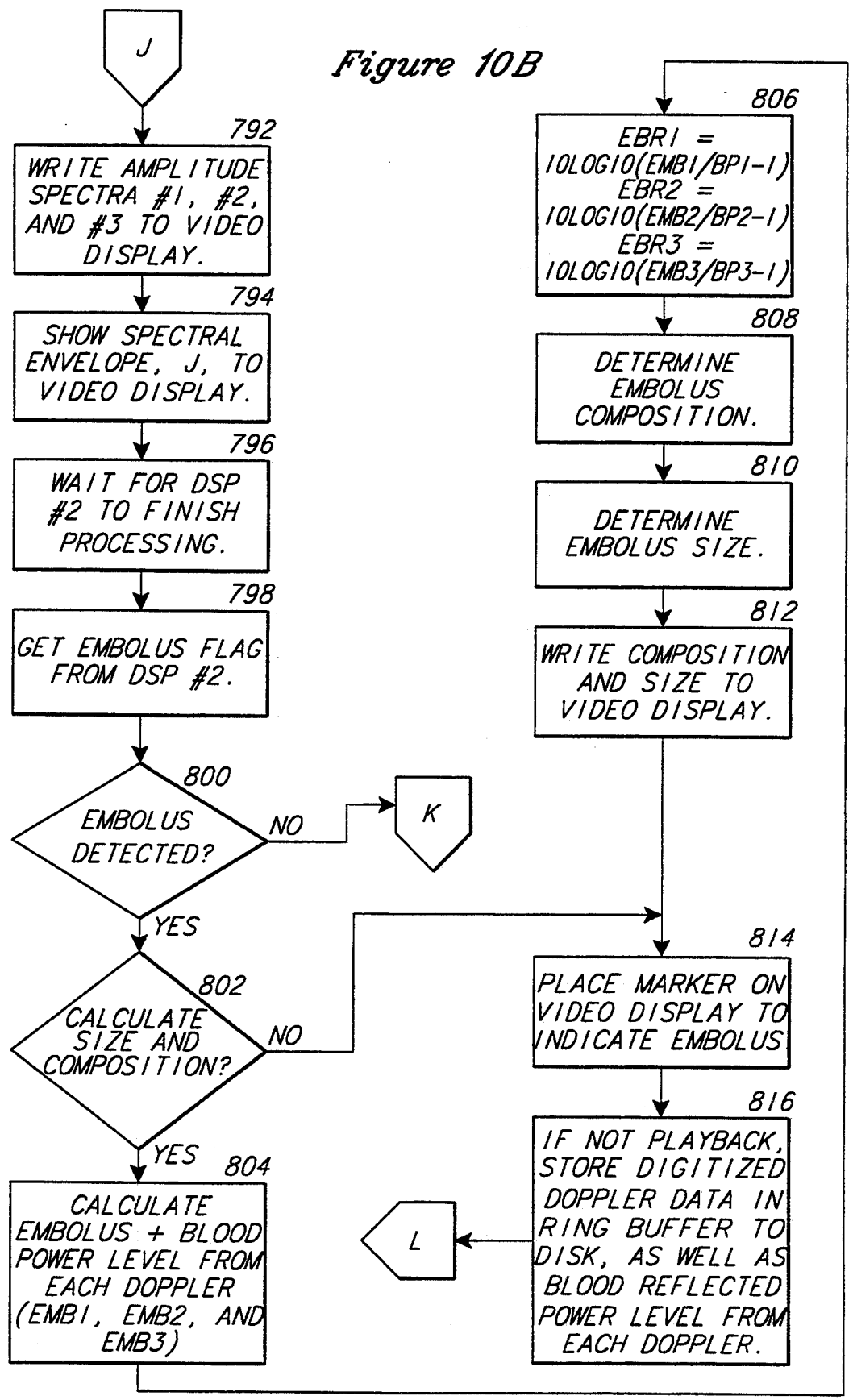
Figure 10C:
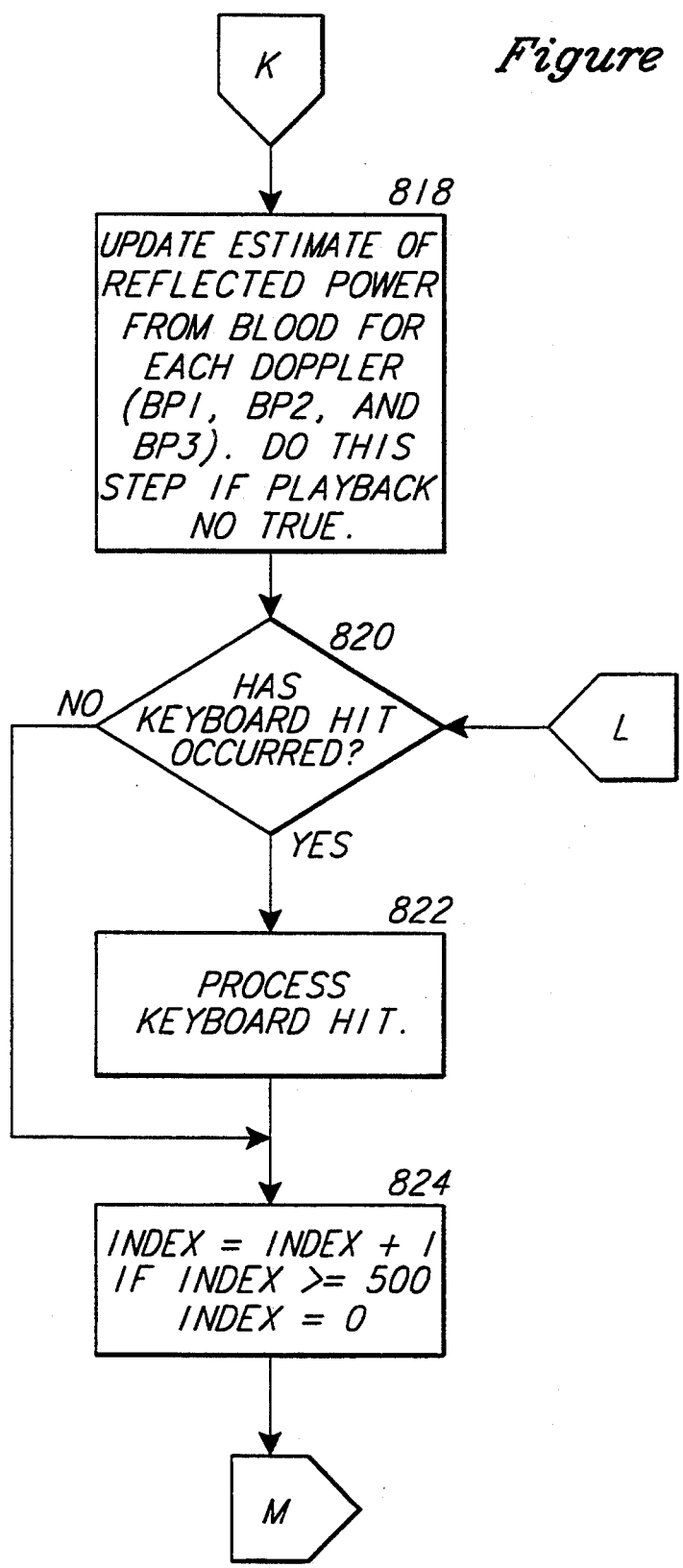
Figure 11A:
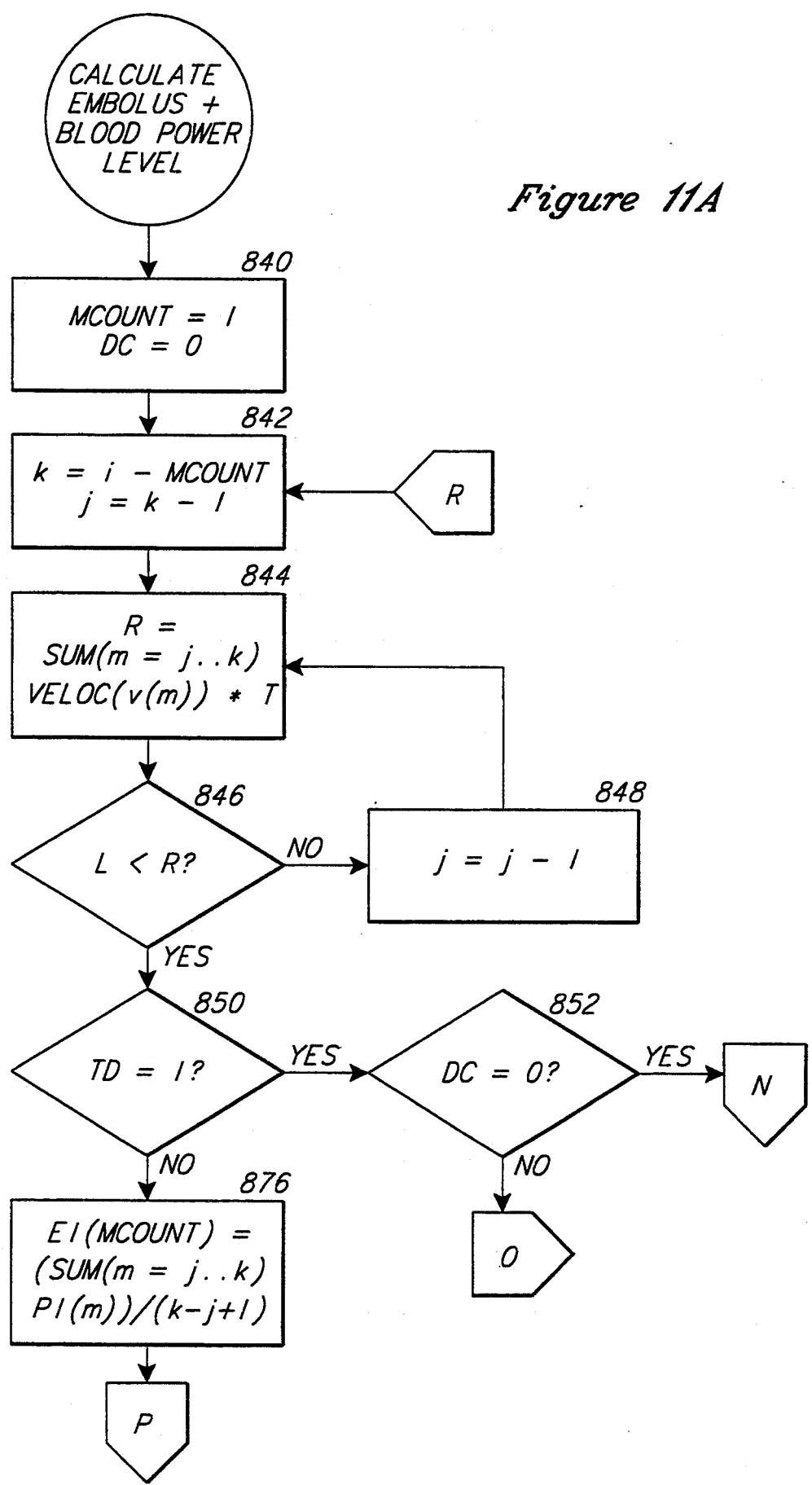
FIG. 11 is a flow chart of a subroutine used in the host computer software of FIG. 10 for calculating the ultrasonic backscattered power from the blood flow under study when an embolus and blood are present in the sample volume.
Figure 11B:
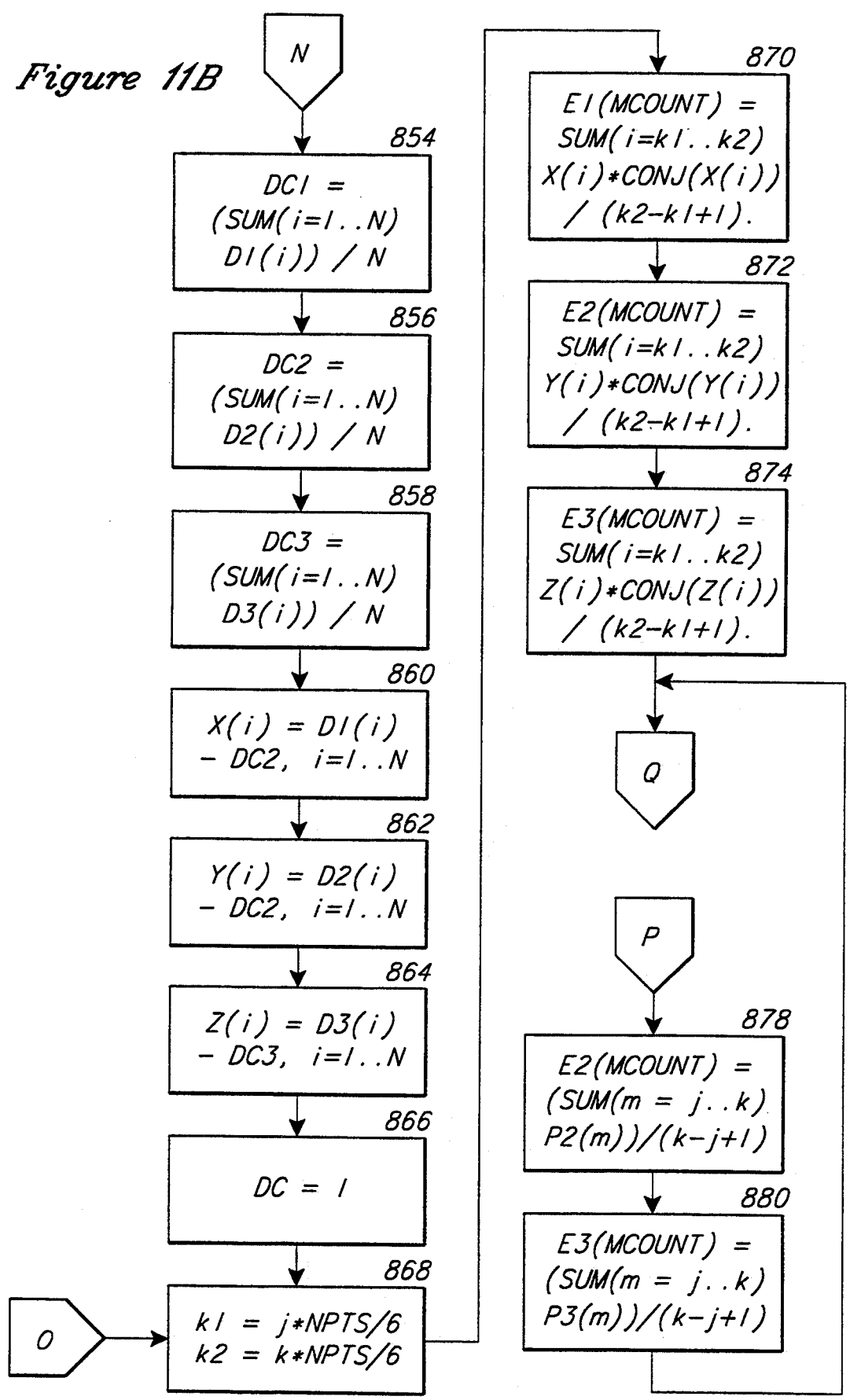
Figure 11C:
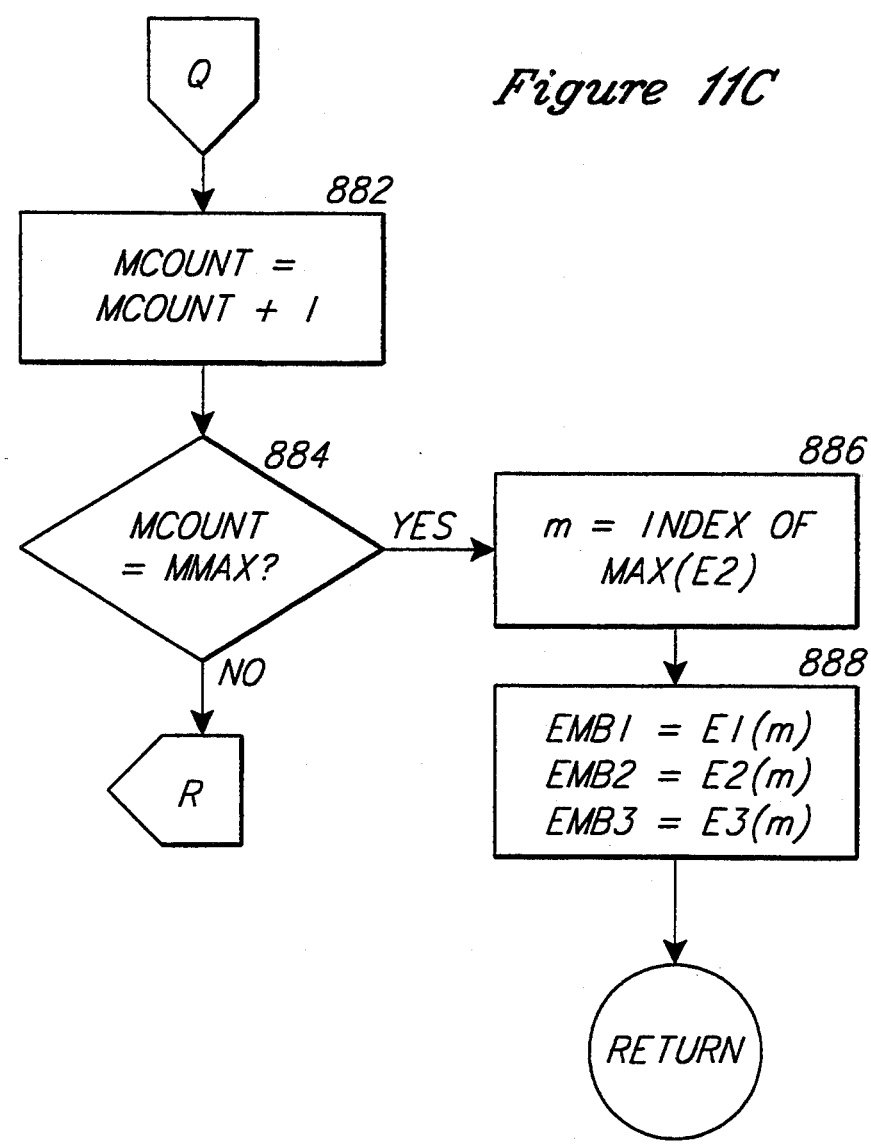
Figure 12A:
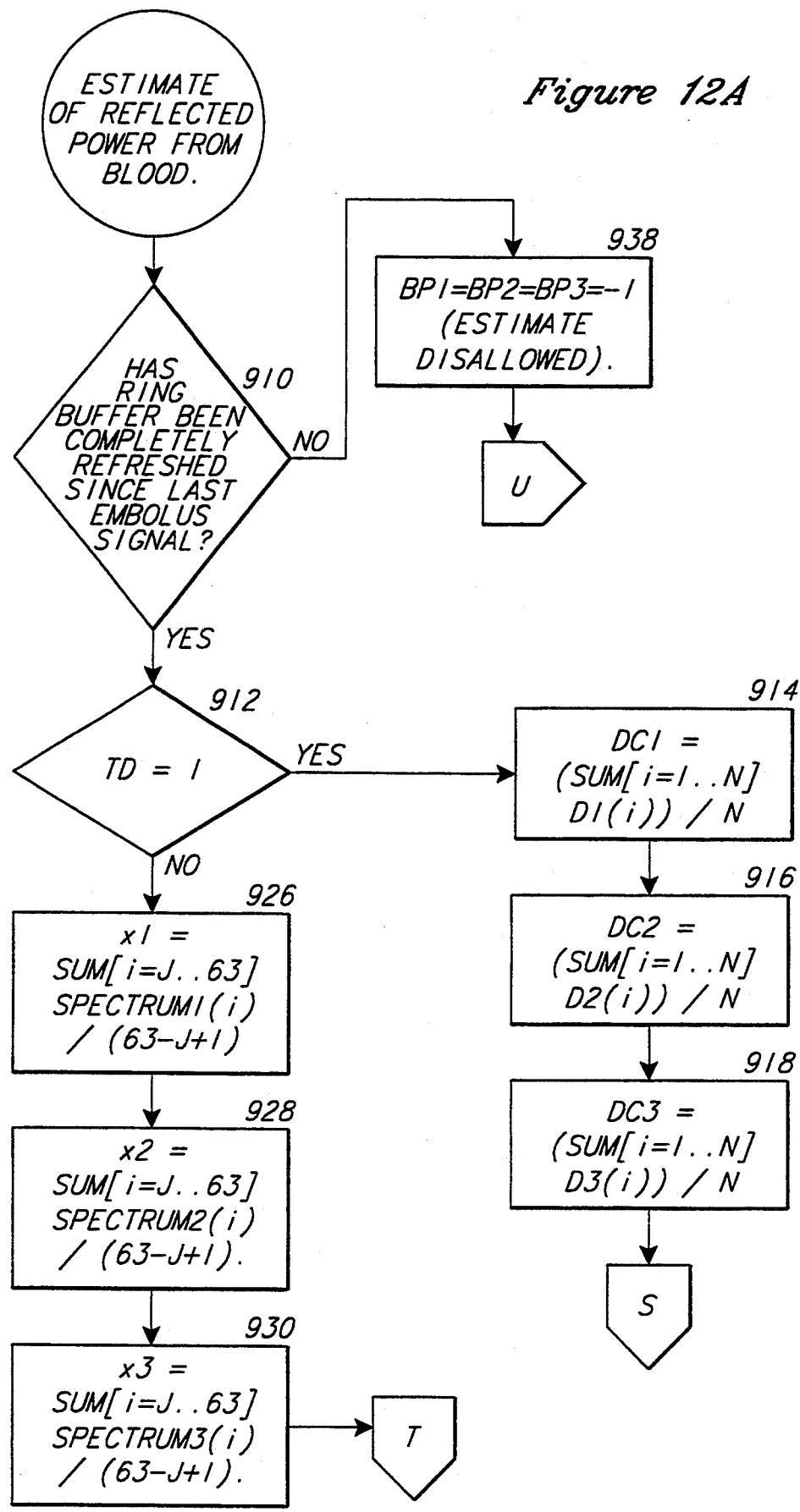
FIG. 12 is a flow chart of a subroutine used in the host computer software of FIG. 10 for calculating the ultrasonic backscattered power from the blood flow under study when only blood is present in the sample volume.
Figure 12B:
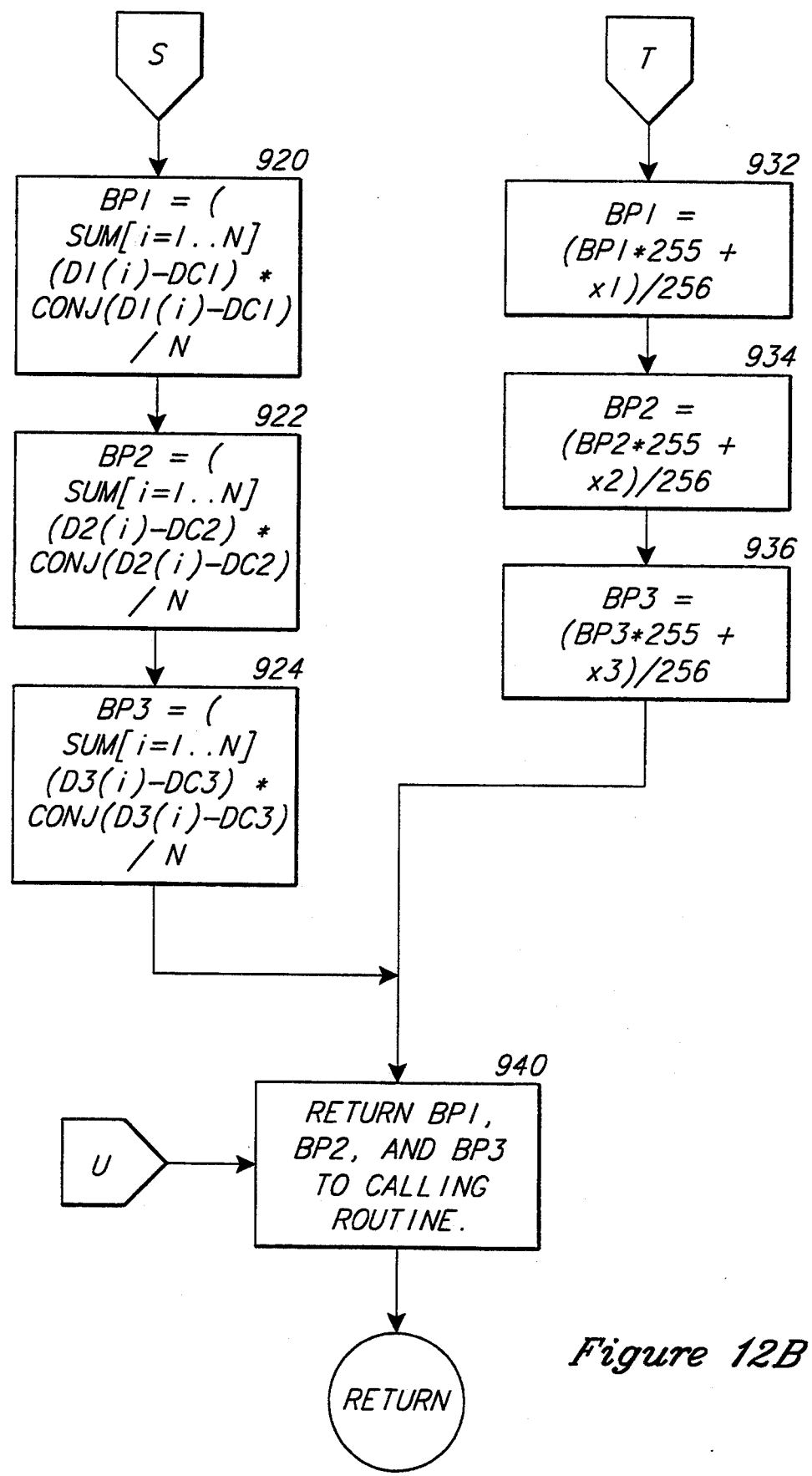
Figure 13:
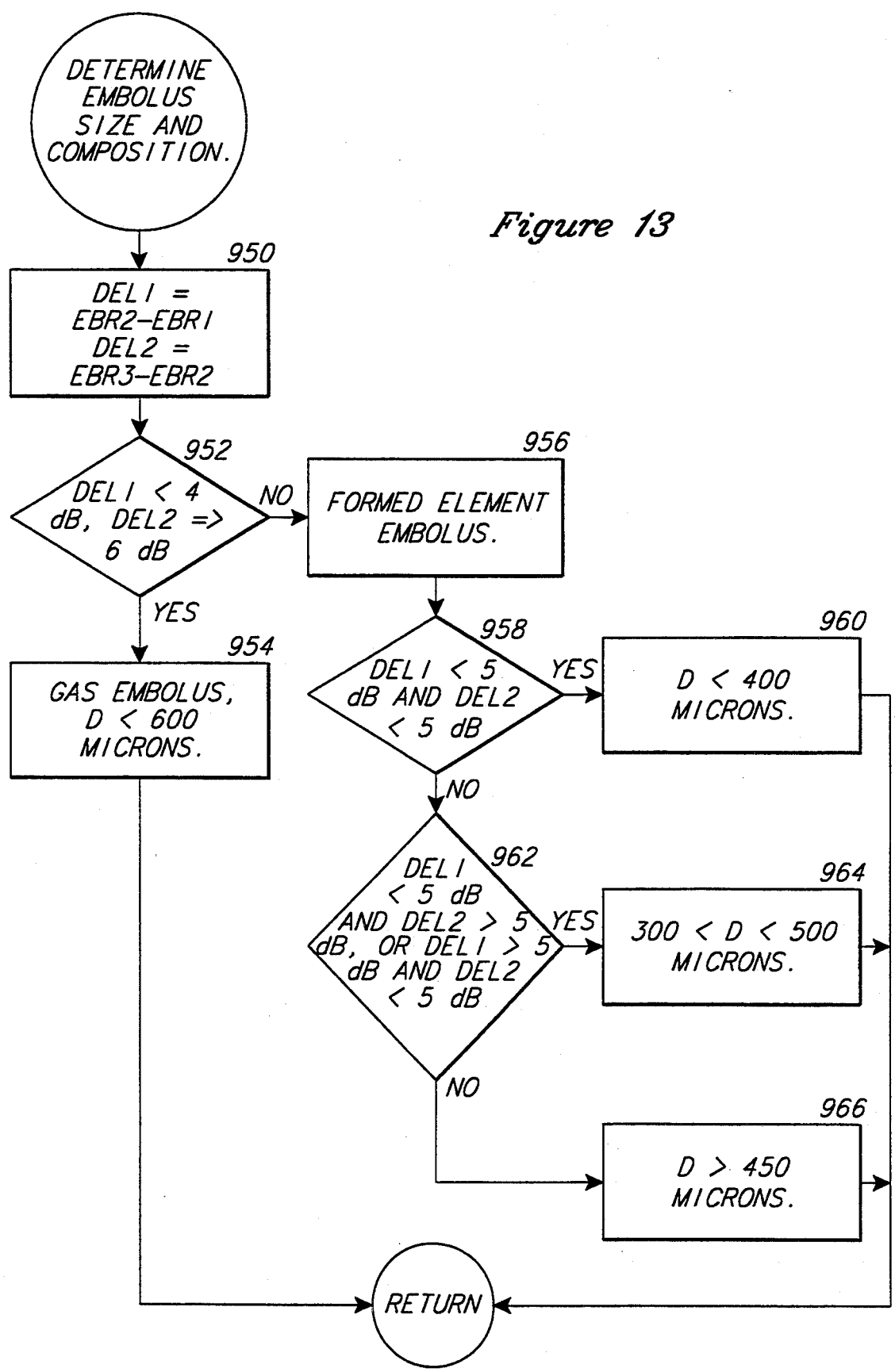
FIG. 13 is a flow chart of a subroutine used in the host computer software of FIG. 10 for distinguishing between a gas bubble embolus and a formed element embolus, and, if the embolus is a formed element, determining the embolus size.
Figure 14A:
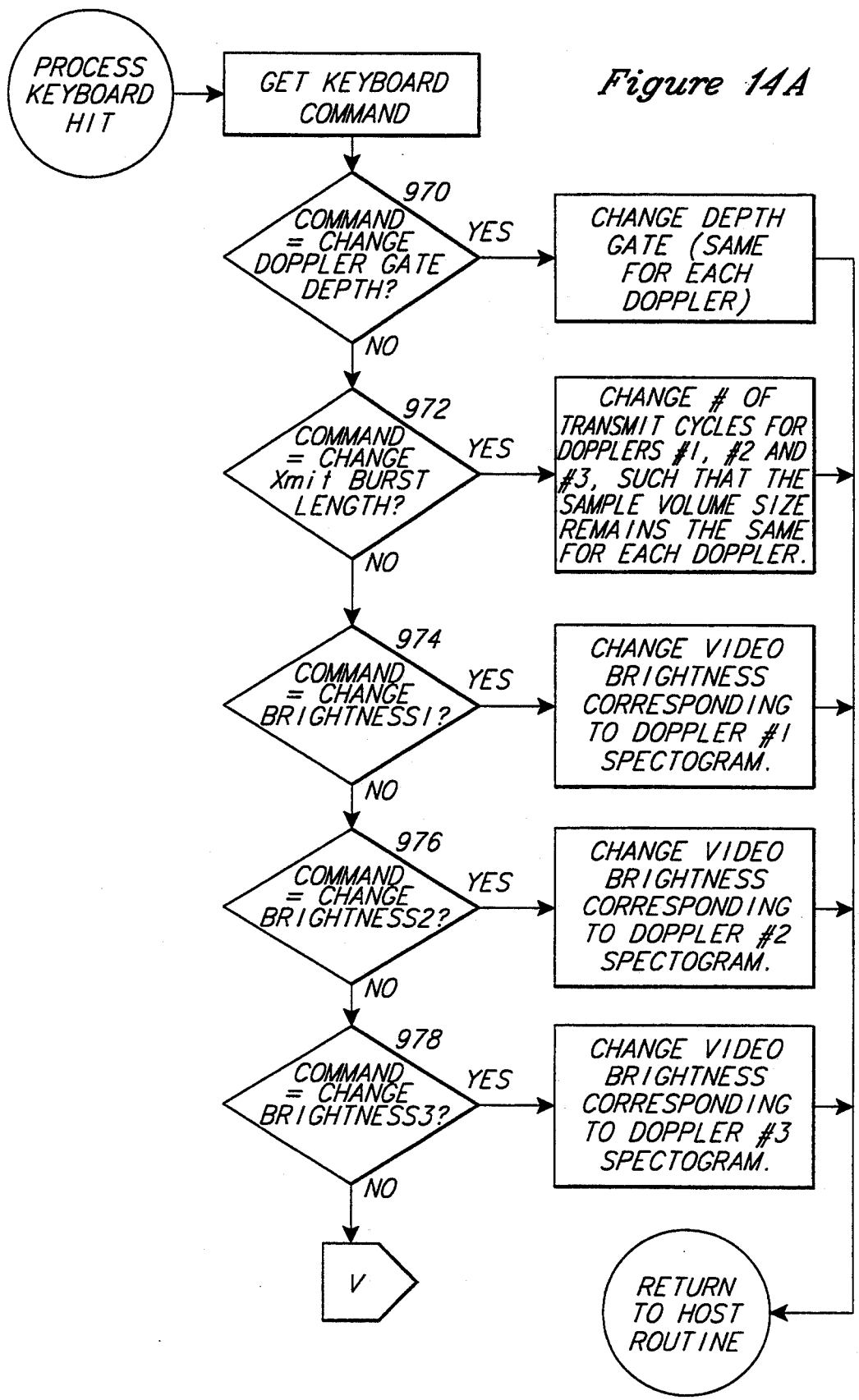
FIG. 14 is a flow chart of a keyboard input subroutine used in the host computer software of FIG. 10 for servicing inputs from a host computer keyboard in the embodiment of FIG. 1.
Figure 14B:
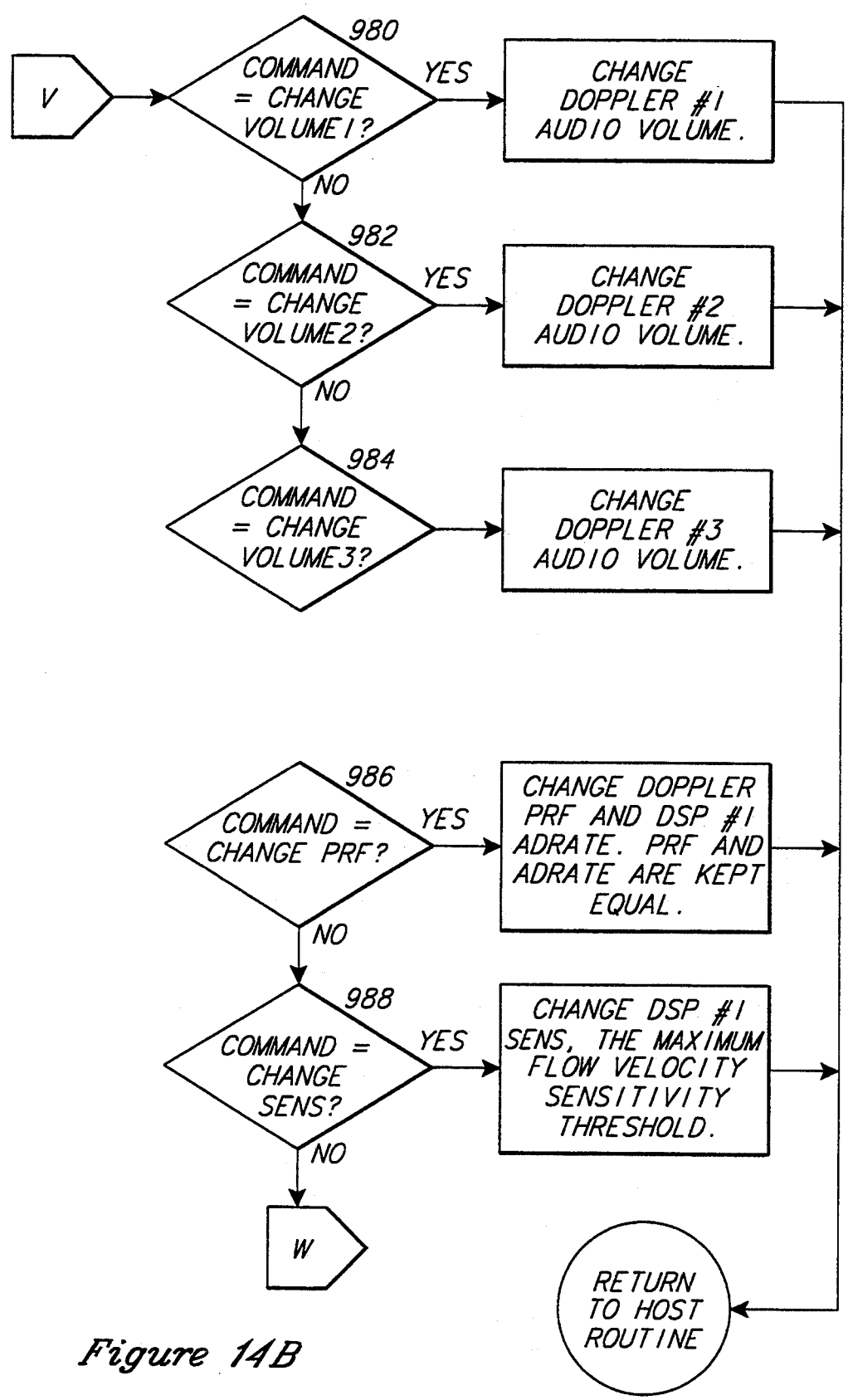
Figure 14C:
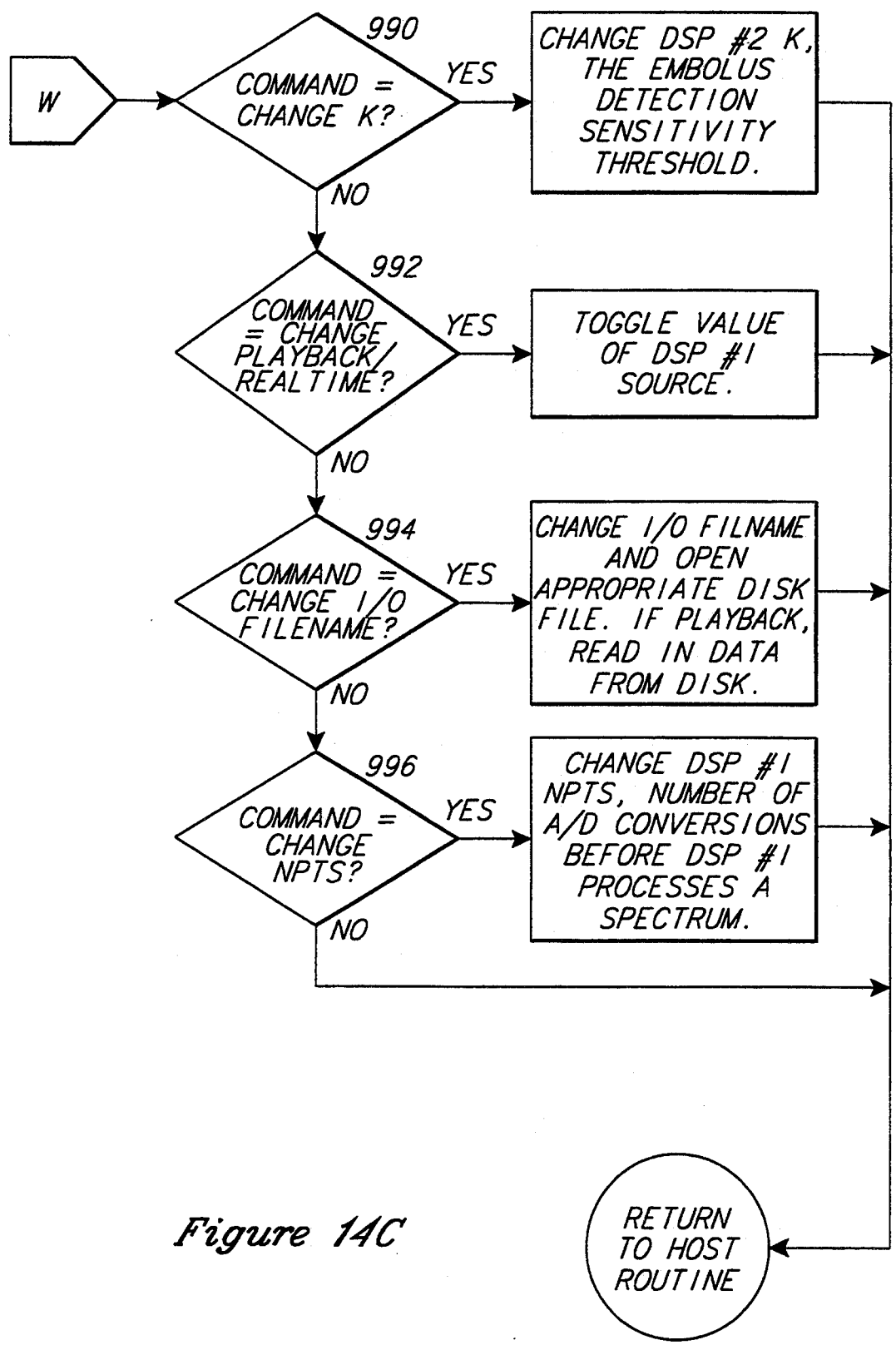

The software controlling the Host computer 400 is described in FIGS. 10, 11, 12, 13 and 14. FIG. 10 is a flow chart of the high-level software. FIGS. 11 through 14 explain subroutines called by the high-level software shown in FIG. 10. FIG. 11 illustrates a subroutine for calculating the Doppler shift signal power level when both embolus and blood are present in the sample volume. FIG. 12 illustrates a subroutine for calculating the Doppler shift signal power when only blood is present in the sample volume. FIG. 13 illustrates a subroutine for discriminating embolus composition (gas or solid) and calculating embolus size, and FIG. 14 illustrates the keyboard service subroutine for interaction with the user.

High-Level Host Computer Software Of FIG. 10

The high-level subroutine of FIG. 10 begins by initializing the DSPs and the Doppler units at step 770. Acquisition and processing parameters are written to DSP1 200 (FIG. 1) at 772 and to DSP2 300 at 774. A loop is then entered at 776 that is controlled only by keyboard input from the user. The software determines at 776 if the user has selected the "Playback" mode in order to play back previously digitized signals. If so, the Host computer 400 loads digitized Doppler shift data from a RAM buffer to DSP1 200 at 778, and alerts DSP1 to the presence of this data by buffer 290 (FIG. 1). Otherwise, DSP1 200 acquires data from the A/D 220. The Host computer 400 then waits at 780 for DSP1 200 to complete processing the three spectra and the maximum forward flow velocity, J. When DSP1 200 indicates via buffer 290 that data is ready for the Host computer 400, the Host computer 400 reads from Host BIFO 1 Doppler shift data at 782, and it reads power spectra for Doppler units 110, 120, 130 and J at 784. J is stored to the array V[INDEX], where INDEX indicates the video display and RAM buffer storage position for the current spectra.

The Host computer 400 subsequently follows a sequence of steps that display the data most recently processed by DSP1 200, and further process this same data to detect and characterize emboli. Under the maximum flow peak for each forward flow spectrum, a full-width, half-maximum average coefficient is calculated at 786. These averages are stored in the arrays P1[Index], P2[Index] and P3[Index]. Amplitude spectra for Doppler units 110, 120, 130 are found by lookup table from power spectra 1, 2 and 3 at step 788. Amplitude spectrum 1, with J, is written to DSP2 300 for the purpose of embolus detection at 790. Then all three amplitude spectra are written to the video display at 792, and the maximum flow velocity J is written to the video display at 794. The Host computer 400 then waits at 796 for response from DSP2 300 as to whether or not an embolus is present in the sample volume. When the DSP2 outputs an EMBOLUS flag as described above, the flag is read at 798.

The software detects that the EMBOLUS flag is TRUE at 800, and then determines at 802 whether the size and composition of the embolus is to be calculated. If so, the subroutine for calculating the embolus plus blood power level is called at 804, and the EBR associated with each Doppler (EBR1, EBR2, EBR3) is calculated at 806. From these EBR values, the composition and embolus size are calculated by calling appropriate subroutines at 808 and 810. The composition and embolus size data are then shown to the display at step 812.

It may not be desirable to characterize the emboli while data are being acquired because such calculation may prevent the Host computer 400 from keeping up with the output of DSP1 200, thereby losing Doppler shift signals. It is thus possible to disable this characterization until playback of the acquired Doppler signals 802. In this case, the software determines at 802 that the size and composition of the embolus are not to be calculated, and branches to step 814. The software will also progress to 814 from step 812 after the size and composition of the embolus have been calculated.

At 814, a marker indicative of an embolus is generated on the display, and corresponding signals are stored at 816. The keyboard is then tested at 820 to determine if a keyboard entry is being made. If so, a keyboard interrupt subroutine is called at 822 before progressing to step 824. Otherwise, the software jumps directly from 820 to 824 where the value of INDEX is determined before repeating the loop by returning to 776. At 824, INDEX is incremented by 1 until it reaches a value of 500 at which point it is set equal to zero.

If the software determines at 800 that the EMBOLUS flag has not been set TRUE, then the software calls a subroutine at 818 for updating its calculations of the Doppler shift signal power due to blood without emboli flowing through the sample volume, and the keyboard is tested at 820 and any input is processed at 822 before repeating the loop through 776.

Blood+Embolus Reflection Power Calculating Subroutine Of FIG. 11

FIG. 11 is a flow chart of the subroutine called at 804 (FIG. 10) for calculating the Doppler shift signal power from each Doppler when an embolus plus blood is present in the sample volume. For this calculation, it is necessary to determine a time window within which the best estimate of the average power of signals from embolus plus blood is to be found. This determination not only means finding where the time window should be positioned, but as well, the length of the time window. If the time window is too long, then it will include times during which the embolus is not in the sample volume, and the embolus plus blood power level will be underestimated. If the time window is improperly positioned, the power estimate may be compromised for the same reason. To avoid these problems, the end-position of the time window is consecutively stepped through the region containing the embolic signal. The length of the time window is determined by the minimum amount of time that an embolus would be present in the sample volume, given the current velocity profile. i.e., the length of time is the integral with respect to time of the maximum flow velocity, v(INDEX), calculated at 784 (FIG. 10). When the integral of V(INDEX) with respect to time is equal to the sample volume length, L, then the integration starting and ending points demarcate a time period during which the fastest moving particles in the sample volume traverse the entire sample volume length. If the embolus travels slower than the maximum flow velocity, then the time period between the integration endpoints will be shorter than that during which embolic signals are present. But the danger of including all of the embolic signals in the time period, plus signals which do not include an embolus, is avoided. The desired power estimate is taken as the maximum from all the time windows evaluated.

The subroutine illustrated in FIG. 11 steps backwards in time using the variable MCOUNT, which is initially set to 1 at step 840. The variable DC is set to zero at step 840, indicating that the DC signal component has yet to be subtracted from each Doppler. If i is the time index shortly after detecting an embolic signal, then each value of MCOUNT is used at 842 to determine a new window ending point according to the formula k=i-MCOUNT. The window starting point, j, is also initially set to k−1 at 842. The maximum flow velocity is then integrated backwards (in time) at 844 until the integration value "R" equals the sample volume length, "L." The subroutine determines whether R<L at step 846, and, if not, j is decremented at 848 and the integration is reevaluated at 844. The variable "T" is set equal to the time between velocity samples at 844.

The indices j and k are respectively the starting and ending points for the window over which to find average power. The subroutine checks the value "TD" at 850 to determine whether the average power is to be determined in the time domain (TD=1) or the frequency domain (TD=0). If the calculation is to be done in the time domain, the digitized Doppler shift signal is calculated once starting at 852. When the subroutine first reaches step 852, it will branch to step 854 since the variable "DC" was set to 0 at 840, as explained above. The average complex signal value is determined for Doppler unit 1 at 854, Doppler unit 2 at 856, and Doppler unit 3 at 858. The DC components for Doppler units 1, 2 and 3 are then subtracted from the Doppler shift signals for each Doppler unit at 860, 862, and 864 to form the new arrays X, Y, and Z, respectively. The value "DC" is then set to 1 at 866 to prevent this subtraction from happening more than once.

The signal power for each Doppler is calculated at 868 by first setting the time series window limits k1 and k2. These are different from j and k because the velocity time series used in determining the points j and k contains 1 value for every NPTS values of the Doppler shift time series signal. The division of 6 in step 868 occurs because the three complex Doppler time shift signals are multiplexed into one buffer.

The average power (the mean of the complex signal times its complex conjugate) is calculated for Doppler unit 1 at 870, Doppler unit 2 at 872 and Doppler unit 3 at 874. These average power values are then placed in the arrays E1(mcount), E2(mcount) and E3(mcount), respectively.

If the calculation is to be done in the frequency domain (i.e., "TD" was found to be 0 at 850), then the power already calculated in variables P1(j .. k), P2(j .. k) and P3(j .. k) at 786 (FIG. 10) are averaged for Doppler unit I at 876, Doppler unit 2 at 878, and Doppler unit 3 at 880, and stored respectively in E1(mcount), E2(mcount) and E3(mcount).

The next time window is then initiated by setting a new value of MCOUNT at 882, and making sure at 884 that MCOUNT has not exceeded a maximum value, MMAX. MMAX is an integer value that needs to be large enough such that the integration window at MCOUNT=MMAX includes Doppler shift signals from blood with no embolus present. This insures that the power estimates in E1(), E2() and E3() look far enough back in time to where the embolus first appeared. If the subroutine determines at 884 that MMAX has not been exceeded, then the new window is evaluated at 842. If the subroutine determines at 884 that MMAX has been exceeded, then the index, m, of the window with maximum power for Doppler unit 1 is calculated at 886, and the power corresponding to this index for each Doppler unit is placed in the variables EMB1, EMB2 and EMB3 at 888. EMB1, EMB2 and EMB3 are returned to the calling routine.

Blood Reflection Power Calculating Subroutine For Of FIG. 12

A flow chart of the subroutine called at 804 (FIG. 10) for calculating the Doppler shift signal power from each Doppler unit when blood without an embolus is present in the sample volume is illustrated in FIG. 12. This calculation starts at step 910 by insuring that the RAM buffer 420 has been completely overwritten with new data since the last embolus was detected. If this is not the case then the estimate is designated as being disallowed by placing −1 into each power estimate at 938. These estimates are then returned to the calling routine 940 before exiting to the calling routine.

If the subroutine determines at 912 that the RAM buffer 420 has not been completely overwritten with new data, the subroutine branches to 912 to determine if the calculation of Doppler shift signal power from blood is to be done in either the time domain or the frequency domain. The calculation is done in the time domain if "TD" is found at 912 to be equal to 1, and it is done in the frequency domain if "TD" is found at 912 to be equal to 0. If the calculation is to be done in the time domain, the digitized DC Doppler shift signal is calculated for Doppler unit 1 at 914, for Doppler unit 2 at 916 and for Doppler unit 3 at 918.

This DC Doppler shift is subtracted from the Doppler shift signals as the total power is accumulated for Doppler unit 1 at 920, for Doppler unit 2 at 922, and for Doppler unit 3 at 924. The average signal powers for Doppler units 1, 2 and 3 are respectively placed in the variables BP1 at 920, BP2 at 922, and BP3 at 924.

If the calculation is to be done in the frequency domain (i.e., "TD" was found at 912 to be equal to 0), x1, x2, and x3, the average power between zero velocity and the maximum flow velocity for each Doppler unit from the three power spectra most recently obtained from DSP1, are calculated at 926, 928, and 930, respectively. These average powers x1, x2, and x3 are then included in a cumulative average power for Doppler unit 1 at 932, for Doppler unit 2 at 934, and Doppler unit 3 for 936. The length of the cumulative average is arbitrarily set here at 256 spectra.

Finally, BP1, BP2 and BP3, the cumulative average powers, are returned to the calling routine at 940.

Embolus Size And Composition Determining Subroutine OF FIG. 13

A flow chart of the subroutine called at 808 and 810 (FIG. 10) for determining embolus size and composition is illustrated in FIG. 13. This subroutine is based solely on the EBR estimates from each Doppler unit calculated at 806. The EBR, or "embolus to blood power ratio", is a measure of scattering strength of an embolus relative to that from the volume of flowing blood overlapped by the sample volume. The EBR varies with frequency, and three measurements of the EBR at different carrier frequencies are sufficient to distinguish between formed element and gas emboli, and, if an embolus is formed element, to categorize its size. The system here has a 72 dB dynamic range at the A/D converter, and this is considered highly desirable for performing characterization described in this subroutine. It is assumed here that the bubbles or formed elements in question are less than 0.6 nun in diameter. As noted earlier, proper choice of carrier frequencies is important for separating formed element emboli from gas bubbles. Different choices for carrier frequencies will be made based on the design criteria such as which vessels will be interrogated, and the maximum expected embolus size. Such choices will also cause the characterization rules to vary. Illustrated here are the characterization rules for the three frequencies [2.0, 1.714 and 1.2] MHz for Doppler units 1, 2 and 3.

Two parameters, Del1 and Del2, which are used to both characterize and size emboli, are calculated at 950 as Del1=EBR2−EBR1 and Del2=EBR3−EBR2. These parameters Del1 and Del2 are thus a measure of the difference in the scattering of the ultrasound between different Doppler units 110, 120, and 130. The magnitude of these parameters are then compared to specific power thresholds at 952. If Del 1 is less than 4 dB and Del2 is greater than 6 dB the subroutine branches to 954 to indicate the presence of a gas embolus having a diameter D of less than 600 microns. No other size estimation is possible from these measurements, other than the original assumption that the embolus is less than 600 microns in diameter 954. If the subroutine determines at 952 that If either Del1 is not less than 4 dB or that Del2 is not greater than 6 dB, then the subroutine branches to 956 to provide an indication at 956 that a formed element embolus (fat or red cell thrombus) is present.

If a formed element embolus is indicated, then the subroutine determines at 958 if Del1<5 dB and Del2<5 dB. If so, the subroutine branches to 960 to provide an indication that the embolus has a diameter of less than 400 microns. Otherwise, the subroutine branches to 962 where a second comparison is made. The subroutine determines at 962 if either Del1<5 dB and Del2>5 dB or Del1>5 dB and Del2<5 dB. In either case, the subroutine branches to 964 to provide an indication at that the embolus has a diameter in the range 300 to 500 microns. If neither of these conditions are found to be present at 962, the subroutine branches to 966 to provide an indication at that the embolus has a diameter that exceeds 450 microns.

Keyboard Input Subroutine Of FIG. 14

A flow chart of the subroutine called at 822 (FIG. 10) for managing user input from the keyboard is shown in FIG. 14. It will be understood that a variety of such subroutines, in addition to the routine described herein, may be used. The user requests are preferably served in an expedient fashion to minimize the amount of time spent away from the main task of the machine, which is detecting and characterizing emboli in flowing blood. Some of the parameters that may be selected by the keyboard includes:

Pulse Doppler gate depth detected at 970 and implemented at 971

Pulse Doppler transmit burst length detected at 972 and implemented at 973.

Brightness level for spectrogram 1 detected at 974 and implemented at 975, for spectrogram 2 detected at 976 and implemented at 977, and for spectrogram 3 detected at 978 and implemented at 979.

Audio volume for Doppler unit 1 detected at 980 and implemented at 981, for Doppler unit 2 detected at 982 and implemented at 983, and for Doppler unit 3 detected at 984 and implemented at 985.

Doppler pulse repetition frequency detected at 986 and implemented at 987.

Sensitivity threshold for maximum flow velocity estimation detected at 988 and implemented at 989.

Sensitivity threshold for embolus detection detected at 990 and implemented at 991.

Realtime mode or playback mode switch detected at 992 and implemented at 993.

I/O file name detected at 994 and implemented at 995.

NPTS, the number of points between hardware interrupts detected at 996 and implemented at 997. This parameter is particularly useful in playback mode, for elongating embolic signals with respect to time for a more detailed examination of the signal. This is accomplished by decreasing the value of NPTS, which in turn increases the number of spectrogram lines per second, and the number of common data values between adjacent FFT input buffers.

Means To Locate The Embolic Source

Prime sites for detection of emboli to the cerebral circulation are the carotid and vertebral arteries in the neck (the common carotid artery [CCA], the internal carotid artery [ICA], the vertebral arteries [VA]) and the intracranial arteries (middle cerebral arteries [MCA], internal carotid artery [ICA], basilar artery [BA] and vertebral arteries [VA]).

The source of microemboli, when occurring repeatedly, can be located noninvasively with Doppler ultrasound by monitoring at multiple sites. As examples: if detected bilaterally in the cervical carotids or both MCAs, the source is from the heart or ascending aorta; if detected only unilaterally in one of the patient's carotid arteries or a branch thereof, the source is not cardiac and the source can be further delineated by the level below and above which the emboli do or do not occur; i.e., if detected in the cervical ICA and not in the corresponding CCA, the source is between the two levels and around the bifurcation of the CCA; if detected in the MCA and not in the cervical carotid, the source is from the ICA siphon.

By similar techniques, the source of multiple emboli in a given patient can be located to any degree depending on how many sites are monitored either sequentially or by the use of simultaneous multiple probes. The source may be automatically reported by entering the presence of emboli in multiple fields of the computer which incorporate a form of the above subroutine and prints or displays a summary interpretation for use of the patient's managing physician. A useful form for laboratory personnel is illustrated in FIGS. 15A and 15B for two types of patients: a) the patient with a unilateral cerebral symptom such as a TIA or stroke (FIG. 15A), and b) patient with a probable cardiac source or with bilateral cerebral vascular symptoms or episodic dizziness (FIG. 15B).

Figure 15A:
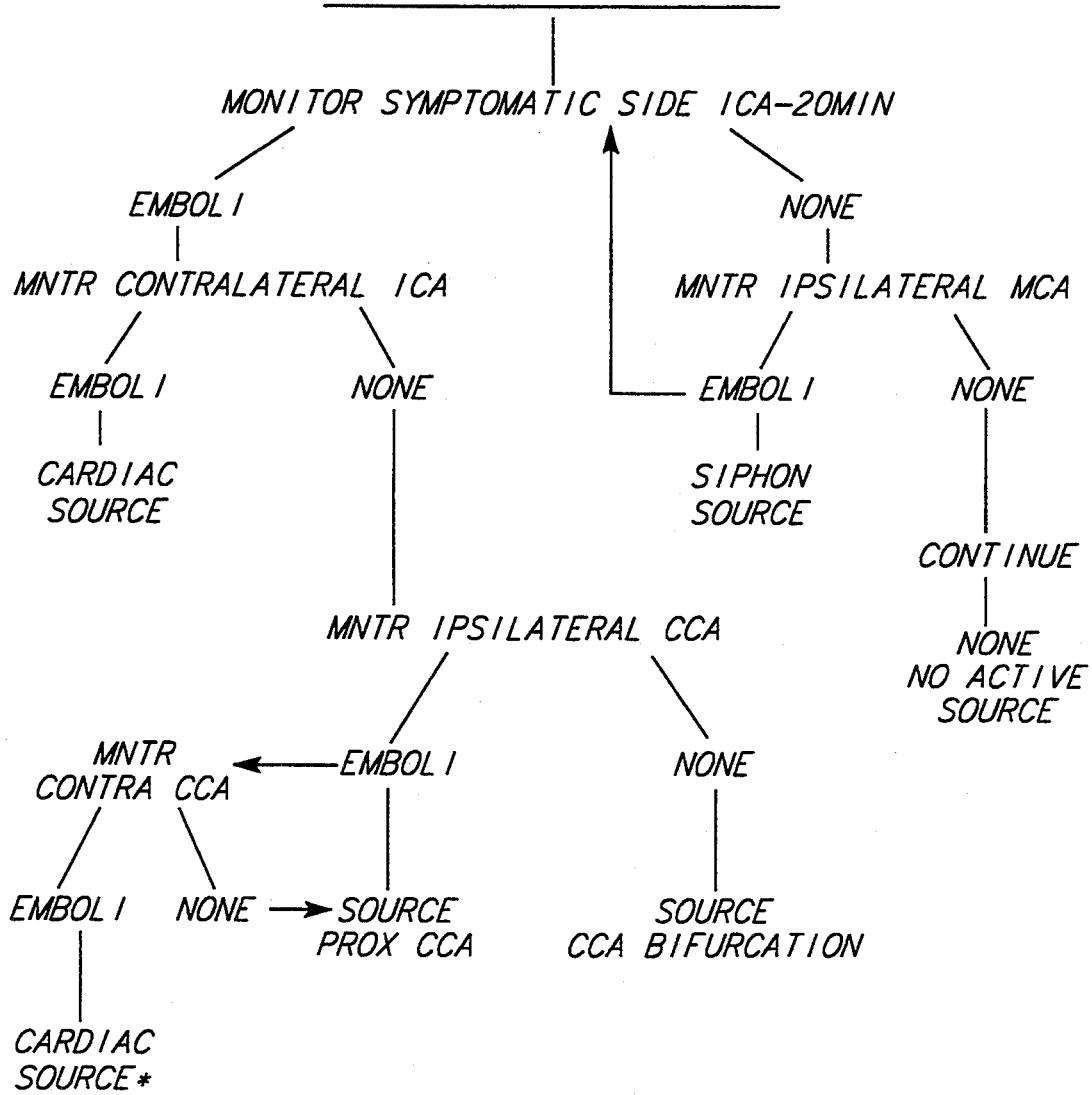
FIGS. 15A and 15B are charts showing a technique for using the inventive system to detect an embolus in a patient during a diagnostic procedure.
Figure 15B:
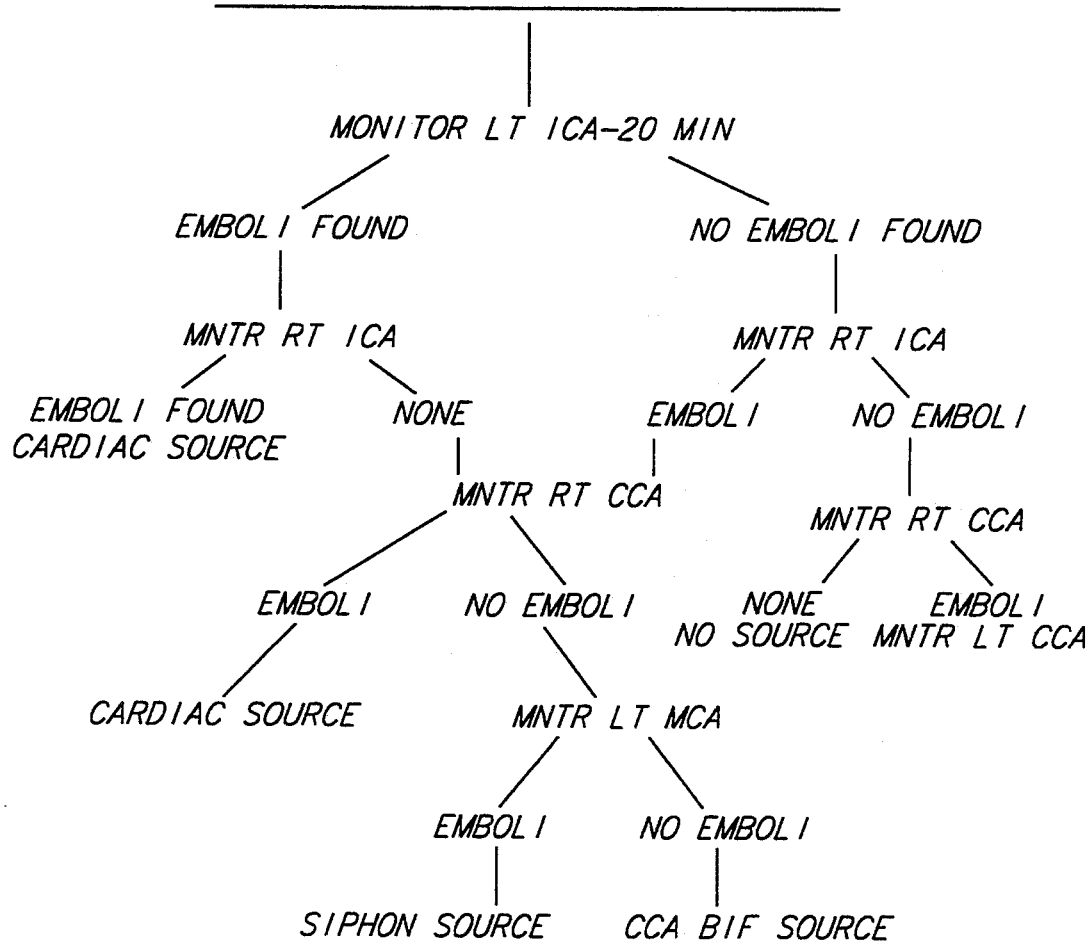

FIG. 15A shows the protocol that should be used for all patients with unilateral CV symptoms. A 2 MHz ultrasonic Doppler is used for both cervical and transcranial arteries. Both directions of the Doppler audio signals are recorded on the audio channels of a recording medium, preferably, a high dynamic range magnetic tape or other recording, i.e., from 25 to 90 dB modulated at −7 to −20 dB. On the Doppler frequency/velocity spectral display a high dynamic range (25 to 90 dB) and a threshold 10 to 25 db should be used depending on the strength of the Doppler signal. The procedure should begin by monitoring a cervical internal carotid artery. The arteries that are monitored are the Internal Carotid Artery (ICA), The Common Carotid Artery (CCA), and the Middle Cerebral Artery (MCA).

The total monitoring time for all arteries should be at least one hour. Ten minutes is the minimum time for monitoring any artery. If there are less than 5 emboli/10 min detected, the monitoring time should be extended. A high embolic rate, i.e. >1/min, requires less time. The rate of embolization (EPH) is calculated for each artery as emboli per hour as follows: EPH=60×emboli/minutes.

It should be noted that bilateral microemboli are necessary to prove a cardiac source, and the term "Cardiac source" means either the ascending aorta or the left side of the heart or, in case of any atrial septal defect, a peripheral venous source. An ASD can be diagnosed by monitoring any one of the carotid arteries and injecting agitated saline or other contrast agent into a peripheral vein and listening for embolic signals in the Doppler signal. The CCA or ICA are preferred monitoring sites because more microemboli may be detected there than in the MCA.

FIG. 15B shows the protocol that should be used for patients with probable cardiac source and those with bilateral cerebrovascular symptom such as dizziness.

It will be understood that the preferred embodiment described herein is simply one example of the practice of the invention and should not be used to limit the following claims. Alternative technology to practice the invention will be readily apparent to one skilled in the art. For example, although the preferred embodiment uses pulse Doppler units, continuous wave Doppler units may also be used, and a single, multiple frequency Doppler unit could be used in place of multiple Doppler units having different frequencies. Similarly, although specific ultrasound frequencies have been described, other ultrasound frequencies could be used. It will also be understood that there is no required spacing between frequency components in a frequency spectrum. Instead, the frequency components in a spectrum can be spaced very closely to each other and, in fact, a continuous frequency spectrum could be used without departing from the spirit of the invention. Similarly, although the preferred embodiment has been described as using "frequency domain" processing, it will be understood that "time domain" processing can also be used.

The word "transducer" as used in the claims is intended to encompass any device for directing ultrasound into blood flow, including a single transducer element and multiple transducers elements mounted either together in a single unit or in physically separate units. Also, the transducer can be configured and/or operated so that the frequency spectra obtained in the practice of the invention represent blood flow at either the same or different locations, as well as blood flow at the same time or different times. The location of the blood flow may be at various locations in the body as well as outside the body in blood flows to such devices as heart/lung machines. Other variations in the preferred embodiment disclosed herein will be apparent to one skilled in the art.

We claim:

1. A system for ultrasonically detecting an embolus in blood flow, comprising:
    an ultrasound transducer positioned in ultrasound communication with said blood flow;
    a Doppler ultrasound unit electrically connected to said ultrasound transducer, said Doppler ultrasound unit generating an output signal having a frequency spectrum indicative of the velocity of ultrasound scatters in said blood flow; and
    signal processing means receiving said output signal from said Doppler ultrasound unit and determining at least one frequency spectrum corresponding to said output signal, each frequency spectrum containing a plurality of frequency components, said signal processing means further detecting the presence of an embolus in said blood as a function of the amplitude of a frequency component obtained at a first time and the amplitude of a a frequency component obtained at a time different from said first time.

2. The ultrasound embolus detection system of claim 1 wherein said processing means determines the frequency of a frequency component corresponding to the maximum velocity of said blood flow, and said processing means then detects said embolus by examining the relationship between only the frequency components of said spectrum that are less than the frequency of the frequency component corresponding to the maximum velocity of said blood flow.

3. The ultrasound embolus detection system of claim 2 wherein said processing means determines the frequency of a frequency component corresponding to the maximum velocity of said blood flow by identifying the highest of one or more frequency components having an amplitude that exceeds a threshold value.

4. The ultrasound embolus detection system of claim 1 wherein said processing means includes artifact detecting means for examining reverse flow frequency components of said spectrum to provide an indication of an artifact condition and for generating an artifact indication responsive thereto, said processing means further inhibiting the detection of an embolus responsive to said artifact indication.

5. The ultrasound embolus detection system of claim 4 wherein said artifact detecting means comprise:
    means for comparing each frequency component of said spectrum corresponding to reverse flow to a threshold; and
    means for causing said processing means to inhibit the detection of an embolus if any of said frequency components of said spectrum corresponding to reverse flow exceed said threshold.

6. The ultrasound embolus detection system of claim 1 wherein said embolus is detected as a function of the relationship between the amplitude of at least two frequency components in the same frequency spectrum.

7. The ultrasound embolus detection system of claim 6 wherein said frequency components are taken from the same sample volume of said blood flow.

8. The ultrasound embolus detection system of claim 1 wherein said Doppler unit is a pulse Doppler unit operating at a predetermined pulse duration, repetition rate, and depth gate.

9. The ultrasound embolus detection system of claim 1 wherein said Doppler ultrasound unit includes range gate means for processing ultrasound reflections from different locations in a blood vessel that is in ultrasound communication with said ultrasound transducer thereby allowing said signal processing means to detect the presence of an embolus at two different locations in said blood vessel.

10. The ultrasound embolus detection system of claim 1 wherein said ultrasound transducer includes first and second ultrasound probes positioned in ultrasound communication with a blood vessel at two spaced apart locations, said Doppler ultrasound unit generating an output signal from each of said ultrasound probes each of which has a frequency spectrum indicative of the velocity of ultrasound scatters in said blood vessel adjacent said probe, and wherein said signal processing means receives both of said output signals and detects the presence of an embolus in the blood vessel at each of said locations as a function of a relationship between the amplitude of one frequency component and the amplitude of another frequency component in each of said frequency spectra whereby said system is capable of detecting the presence of an embolus at two different locations in said blood vessel.

11. The ultrasound embolus detection system of claim 1 wherein said frequency component obtained at said first time is at a different frequency from said frequency component obtained at said different time.

12. A system for ultrasonically detecting an embolus in blood flow, comprising:

an ultrasound transducer positioned in ultrasound communication with said blood flow;

a Doppler ultrasound unit electrically connected to said ultrasound transducer, said Doppler ultrasound unit generating an output signal having a frequency spectrum indicative of the velocity of ultrasound scatters in said blood flow; and signal processing means receiving said output signal from said Doppler ultrasound unit and determining at least one frequency spectrum corresponding to said output signal, each frequency spectrum containing a plurality of frequency components, said signal processing means further detecting the presence of an embolus in said blood as a function of the amplitude of one frequency component and the amplitude of another frequency component, said processing means further comparing the amplitude of at least one frequency component to a threshold, and then providing an indication of an embolus if said amplitude exceeds said threshold.

13. The ultrasound embolus detection system of claim 12 wherein said processing means compares an average of the amplitudes of a plurality of adjacent frequency components to said threshold to provides an indication of an embolus.

14. A system for ultrasonically detecting an embolus in blood flow, comprising:

an ultrasound transducer positioned in ultrasound communication with said blood flow;

a Doppler ultrasound unit electrically connected to said ultrasound transducer, said Doppler ultrasound unit generating an output signal having a frequency spectrum indicative of the velocity of ultrasound scatters in said blood flow; and signal processing means receiving said output signal from said Doppler ultrasound unit and determining at least one frequency spectrum corresponding to said output signal, each frequency spectrum containing a plurality of frequency components, said signal processing means further detecting the presence of an embolus in said blood as a function of the amplitude of one frequency component and the amplitude of another frequency component, said processing means further detecting an embolus only if the amplitude of one frequency component is greater than a threshold and the amplitude of a second frequency component is less than a threshold.

15. The ultrasound embolus detection system of claim 14 wherein said threshold for each frequency component in said spectrum is determined as a function of the amplitudes of the same frequency component in a plurality of spectra obtained at an earlier point in time.

16. The ultrasound embolus detection system of claim 14 wherein said processing means compares a plurality of frequency component pairs to said threshold and counts the number of times that one frequency component in each pair is greater than said threshold and the amplitude of the other frequency component in said pair is less than said threshold, said processing means detecting an embolus only if said count is greater than a predetermined value.

17. The ultrasound embolus detection system of claim 14 wherein said processing means sets said threshold as a function of the amplitude of at least one frequency component in a second spectrum taken at a time that is different from when the other of said spectrum was obtained.

18. The ultrasound embolus detection system of claim 17 wherein said processing means determines said second spectrum from said output signal taken after the output signal from which the other of said spectrum was determined.

19. A system for ultrasonically detecting an embolus in blood flow, comprising:

an ultrasound transducer positioned in ultrasound communication with said blood flow;

a Doppler ultrasound unit electrically connected to said ultrasound transducer, said Doppler ultrasound unit generating an output signal having a frequency spectrum indicative of the velocity of ultrasound scatterers in said blood flow; and signal processing means receiving said output signal from said Doppler ultrasound unit and determining at least one frequency spectrum corresponding to said output signal, each frequency spectrum containing a plurality of frequency components, said signal processing means further detecting the presence of an embolus in said blood as a function of the amplitude of one frequency component and the amplitude of another frequency component, said processing means further examining a plurality of frequency component pairs and counting the number of times that the amplitude of one frequency component in each pair has predetermined relationship to the amplitude of the other frequency component in said pair, said processing means detecting an embolus only if said count is greater than a predetermined value.

20. A system for ultrasonically detecting an embolus in blood flow, comprising;

an ultrasound transducer positioned in ultrasound communication with said blood flow;

a Doppler ultrasound unit electrically connected to said ultrasound transducer, said Doppler ultrasound unit generating an output signal having a frequency spectrum indicative of the velocity of ultrasound scatters in said blood flow; and signal processing means receiving said output signal from said Doppler ultrasound unit and determining at least one frequency spectrum corresponding to said output signal, each frequency spectrum containing a plurality of frequency components, said signal processing means further detecting the presence of an embolus in said blood as a function of the amplitude of one frequency component and the amplitude of another frequency component, said processing means further comprising the frequency components in a spectrum to a threshold, and using said frequency components to detect said embolus only if said frequency components exceed said threshold.

21. The ultrasound embolus detection system of claim 20 wherein said threshold is a function of the amplitude of a frequency component in a second spectrum obtained at a time after the other of said spectra was obtained, the frequency component used to determine said threshold bearing a predetermined relationship to the frequency components being compared to said threshold.

22. A system for ultrasonically detecting an embolus in blood flow, comprising:

an ultrasound transducer positioned in ultrasound communication with said blood flow;

a Doppler ultrasound unit electrically connected to said ultrasound transducer, said Doppler ultrasound unit operating at a plurality of different carrier frequencies which examine the same blood flow, said Doppler ultrasound unit generating an output signal having for each carrier frequency a respective frequency spectrum indicative of the velocity of ultrasound scatterers in said blood flow; and signal processing means receiving said output signal from said Doppler ultrasound unit and determining a frequency spectrum corresponding to each of said output signals said signal processing means determining a characteristic of a detected embolus as a function of a relationship between the frequency spectrum for one carrier frequency and the frequency spectrum for another carrier frequency.

23. The ultrasound embolus detection system of claim 22 wherein said Doppler ultrasound unit generates a plurality of different carrier frequencies using a corresponding plurality of Doppler ultrasound units electrically connected to said ultrasound transducer.

24. The ultrasound embolus detection system of claim 22 wherein said Doppler unit is a pulse Doppler unit, and wherein said pulse Doppler unit has the same pulse duration, pulse repetition rate, and depth gate for each carrier frequency.

25. The ultrasound embolus detection system of claim 22 wherein said processing means determines said characteristic as a function of a relationship between the power of the frequency spectrum for one carrier frequency and the power of the frequency spectrum for another carrier frequency.

26. The ultrasound embolus detection system of claim 25 wherein said processing means determines said characteristic as a function of a relationship between the power of only a portion of the frequency spectrum for one carrier frequency and the power of only a portion of the frequency spectrum for another carrier frequency.

27. The ultrasound embolus detection system of claim 25 wherein said processing means further includes:
means for determining a set of first intermediate values, each value in said set corresponding to the power of the frequency spectrum for a respective carrier frequency of ultrasound reflected from blood and an embolus in said blood flow;
means for determining a set of second intermediate values, each value in said set corresponding to the power of the frequency, spectrum for a respective carrier frequency of ultrasound reflected from said blood flow;
means for calculating a set of composite values each of which is a function of the first and second intermediate values determined from the same carrier frequency; and
means for determining a characteristic of said embolus as a function of a relationship between at least two of said composite values in said set.

28. The ultrasound embolus detection system of claim 27 wherein each of said sets contain three values, and wherein said embolus characteristic determining means identifies a characteristic of said embolus as a function of a relationship between two of said composite values and the relationship between one of said two composite values and the remaining composite value.

29. The ultrasound embolus detection system of claim 27 wherein each of said sets contain three values, the first of said composite values being derived from the highest carrier frequency, the third of said composite values being derived from the lowest carrier frequency, and the second of said composite values being derived from a carrier frequency that is intermediate said highest carrier frequency and said lowest carrier frequency.

30. The ultrasound embolus detection system of claim 27 wherein said embolus characteristic determining means determines the size of said embolus by comparing the difference between said first and second composite values to a first threshold, and the difference between said second and third composite values to a second threshold.

31. The ultrasound embolus detection system of claim 27 wherein said embolus characteristic determining means determines the composition of said embolus by comparing the difference between said first and second composite values to a first threshold, and the difference between said second and third composite values to a second threshold.

32. The ultrasound embolus detection system of claim 22 wherein said processing means determines the size of said embolus.

33. The ultrasound embolus detection system of claim 22 wherein said processing means determines the composition of said embolus.

34. The ultrasound embolus detection system of claim 22 wherein said processing means further includes means for scaling the frequency of the components in the spectra for two of said carrier frequencies as a function of the relative values of said carrier frequencies so that the Doppler frequencies derived from said carrier frequencies are scaled to the same velocity value responsive to scatters in said blood flow moving at the same velocity.

35. The ultrasound embolus detection system of claim 22 wherein said Doppler unit operates at one carrier frequency during a period that is different from a period during which said Doppler unit operates at the other carrier frequency.

36. The ultrasound embolus detection system of claim 22 wherein said blood flow passes through a vessel with which said transducer is in ultrasound communication, and wherein said Doppler unit examines blood flow through the same portion of said vessel for each carrier frequency of transmitted ultrasound.

37. The ultrasound embolus detection system of claim 22 wherein said blood flow passes through a vessel with which said transducer is in ultrasound communication, and wherein said Doppler unit examines blood flow through a different portion of said vessel for each carrier frequency of transmitted ultrasound.

38. A system for ultrasonically detecting an embolus in blood flow, comprising:
an ultrasound transducer positioned in ultrasound communication with said blood flow;
a Doppler ultrasound unit electrically connected to said ultrasound transducer, said Doppler ultrasound unit generating an output signal having a frequency spectrum indicative of the velocity of ultrasound scatterers in said blood flow; and
signal processing means receiving said output signal from said Doppler ultrasound unit and determining at least one frequency spectrum corresponding to said output signal, each frequency spectrum containing a plurality of frequency components, said signal processing means detecting said embolus as a function of the relationship between the amplitude of a frequency component in a first frequency spectrum and the amplitude of a frequency component in a second frequency spectrum obtained at a time that is different from when said first frequency spectrum was obtained.

39. The ultrasound embolus detection system of claim 38 wherein said first and second frequency spectra are taken from the same sample volume of said blood flow.

40. A system for ultrasonically detecting an embolus in blood flow, comprising:

an ultrasound transducer position in ultrasound communication with said blood flow;

a Doppler ultrasound unit electrically connected to said ultrasound transducer, said Doppler ultrasound unit generating an output signal having a frequency spectrum indicative of the velocity of ultrasound scatters in said blood flow; and signal processing means receiving said output signal from said Doppler ultrasound unit and determining at least one frequency spectrum corresponding to said output signal, each frequency spectrum containing a plurality of frequency components, said signal processing means further detecting the presence of an embolus in said blood as a function of the amplitude of one frequency component and the amplitude of another frequency component, said processing means further including means for generating a modified frequency spectrum having a plurality of frequency components, each of which is a composite of related frequency components of at least two frequency spectra obtained from said output signal at different times, and wherein at least one of the frequency components that said processing means uses to detect an embolus is a frequency component from said modified frequency spectrum.

41. A system for determining a characteristic of an embolus in a blood flow, comprising:

an ultrasound transducer positioned in ultrasound communication with said blood flow;

a Doppler ultrasound unit electrically connected to said ultrasound transducer, said Doppler ultrasound unit operating at a plurality of different carrier frequencies, said Doppler unit generating an output signal having for each carrier frequency a respective frequency spectrum indicative of the velocity of ultrasound scatterers in said blood flow; and signal processing means receiving said output signal from said Doppler ultrasound unit, said signal processing means determining a characteristic of an embolus in said blood as a function of a relationship between the frequency spectrum for one carrier frequency and the frequency spectrum for another carrier frequency.

42. The ultrasound embolus characteristic determining system of claim 41 wherein said Doppler ultrasound unit generates a plurality of different carrier frequencies using a corresponding plurality of Doppler ultrasound units electrically connected to said ultrasound transducer.

43. The ultrasound embolus characteristic determining system of claim 42 wherein said Doppler ultrasound units are 3 in number.

44. The ultrasound embolus characteristic determining system of claim 42 wherein said Doppler ultrasound units are pulse Doppler ultrasound units having the same pulse duration, pulse repetition rate, and depth gate.

45. The ultrasound embolus characteristic determining system of claim 41 wherein said processing means determines said characteristic as a function of a relationship between the power of the frequency spectrum for one carrier frequency and the power of the frequency spectrum for another carrier frequency.

46. The ultrasound embolus characteristic determining system of claim 45 wherein said processing means determines said characteristic as a function of a relationship between the power of only a portion of the frequency spectrum for one carrier frequency and the power of only a portion of the frequency spectrum for another carrier frequency.

47. The ultrasound embolus characteristic determining system of claim 45 wherein said processing means further includes:

means for determining a set of first intermediate values, each value in said set corresponding to the power of the frequency spectrum for a respective carrier frequency of ultrasound reflected from blood and an embolus in said blood flow;

means for determining a set of second intermediate values, each value in said set corresponding to the power of the frequency spectrum for a respective carrier frequency of ultrasound reflected from said blood flow;

means for calculating a set of composite values each of which is a function of the first and second intermediate values determined from the same carrier frequency; and means for determining a characteristic of said embolus as a function of a relationship between at least two of said composite values in said set.

48. The ultrasound embolus characteristic determining system of claim 47 wherein each of said sets contain three values, and wherein said embolus characteristic determining means identifies a characteristic of said embolus as a function of a relationship between two of said composite values and the relationship between one of said two composite values and the remaining composite value.

49. The ultrasound embolus characteristic determining system of claim 47 wherein each of said sets contain three values, the first of said composite values being derived from the highest carrier frequency, the third of said composite values being derived from the lowest carrier frequency, and the second of said composite values being derived from a carrier frequency that is intermediate said highest carrier frequency and said lowest carrier frequency.

50. The ultrasound embolus characteristic determining system of claim 47 wherein said embolus characteristic determining means determines the size of said embolus by comparing the difference between said first and second composite values to a first threshold, and the difference between said second and third composite values to a second threshold.

51. The ultrasound embolus characteristic determining system of claim 47 wherein said embolus characteristic determining means determines the composition of said embolus by comparing the difference between said first and second composite values to a first threshold, and the difference between said second and third composite values to a second threshold.

52. The ultrasound embolus characteristic determining system of claim 41 wherein said processing means further includes means for scaling the frequency of the components in the spectra for two of said carrier frequencies as a function of the relative values of said carrier frequencies so that the Doppler frequencies derived from said carrier frequencies are scaled to the same velocity value responsive to scatters in said blood flow moving at the same velocity.

53. The ultrasound embolus characteristic determining system of claim 41 wherein said Doppler unit includes a plurality of Doppler ultrasound units operating at a corresponding plurality of different carrier frequencies, and wherein the frequency spectrum from each of said Doppler units are taken from the same sample volume of said blood flow.

54. The ultrasound embolus characteristic determining system of claim 40 wherein said Doppler unit operates at one carrier frequency during a period that is different from a period during which said doppler unit operates at the other carrier frequency.

55. The ultrasound embolus characteristic determining system of claim 41 wherein said blood flow passes through a vessel with which said transducer is in ultrasound communication, and wherein said Doppler unit examines blood flow through the same portion of said vessel for each carrier frequency of transmitted ultrasound.

56. The ultrasound embolus characteristic determining system of claim 41 wherein said processing means determines the size of said embolus.

57. The ultrasound embolus characteristic determining system of claim 41 wherein said processing means determines the composition of said embolus.

58. The ultrasound embolus characteristic determining system of claim 41 wherein said processing means further includes means for generating a modified frequency spectrum having a plurality of frequency components each of which is a composite of related frequency components of at least two frequency spectra obtained from the output signal at different times, and wherein at least one of the frequency components that said processing means uses to detect an embolus is a frequency component from said modified frequency spectrum.

59. The ultrasound embolus characteristic determining system of claim 41 wherein said Doppler ultrasound unit includes range gate means for processing ultrasound reflections from different locations in a blood vessel that is in ultrasound communication with said ultrasound transducer thereby allowing said signal processing means to determine the characteristics of an embolus at two different locations in said blood vessel.

60. The ultrasound embolus characteristic determining system of claim 41 wherein said blood flow passes through a vessel with which said transducer is in ultrasound communication, and wherein said Doppler unit examines blood flow through a different portion of said vessel for each carrier frequency of transmitted ultrasound.

61. The ultrasound embolus characteristic determining system of claim 41 wherein said Doppler unit includes a plurality of Doppler ultrasound units operating at a corresponding plurality of different carrier frequencies, and wherein the frequency spectrum from each of said Doppler units are taken from respective different sample volumes of said blood flow.

62. A method of ultrasonically detecting an embolus in a blood flow, said method comprising:

reflecting ultrasound from ultrasound scatterers in said blood flow;

generating at least one ultrasound frequency spectrum indicative of the frequency of said reflected ultrasound, each frequency spectrum containing a plurality of frequency components indicative of the velocity of ultrasound scatters in said blood flow; and detecting the presence of an embolus in said blood as a function of the amplitude of a frequency component obtained at a first time and the amplitude of a frequency component obtained at a time different from said first time.

63. The method of claim 62 further including the step of comparing the amplitude of at least one frequency component to a predetermined value, and then providing an indication of an embolus if said amplitude exceeds said predetermined value.

64. The method of claim 63 further including the step of comparing an average of the amplitude of a plurality of adjacent frequency components to said predetermined value to provides an indication of an embolus.

65. A method of ultrasonically detecting an embolus in a blood flow, said method comprising:

reflecting ultrasound from ultrasound scatterers in said blood flow;

generating at least one ultrasound frequency spectrum indicative of the frequency of said reflected ultrasound, each frequency spectrum containing a plurality of frequency components indicative of the velocity of ultrasound scatterers in said blood flow;

examining a plurality of frequency component pairs and counting the number of times that the amplitude of one frequency component in each pair has a predetermined relationship to the amplitude of the other frequency component in said pair; and detecting an embolus only if said count is greater than a predetermined value.

66. The method of claim 80 further including the step of comparing the frequency components in a spectrum to a predetermined value, and using said frequency components to detect said embolus only if said frequency components exceed said predetermined value.

67. The method of claim 62 further including the steps of determining a frequency of a frequency component corresponding to the maximum velocity of said blood flow, and then examining the relationship between only the frequency components of said spectrum that are less than the frequency of the frequency component corresponding to the maximum velocity of said blood flow in order to detect said embolus.

68. The method of claim 67 further including the step of identifying the frequency of the highest of one or more frequency components having an amplitude that exceeds a predetermined value to determine the frequency of the frequency component corresponding to the maximum velocity of said blood flow.

69. The method of claim 62 further including the steps of examining reverse flow frequency components of said frequency spectrum to provide an indication of an artifact condition, and inhibiting the detection of an embolus responsive to artifact condition indication.

70. The method of claim 69 wherein said step of examining reverse flow frequency components of said frequency spectrum to provide an artifact condition is accomplished by the steps of:

comparing each frequency component of said spectrum corresponding to reverse flow to a predetermined value; and inhibiting the detection of an embolus if any of said frequency components of said spectrum corresponding to reverse flow exceed said predetermined value.

71. The method of claim 62 wherein said embolus is detected as a function of the relationship between the amplitude of at least two frequency components in the same frequency spectrum.

72. The method of claim 71 wherein said frequency components are taken from the same sample volume of said blood flow.

73. The method of claim 62 wherein said embolus is detected as a function of the relationship between the amplitude of a frequency component in a first frequency spectrum and the amplitude of a frequency component in a second frequency spectrum obtained at a time that is different from when said first frequency spectrum was obtained.

74. The method of claim 73 wherein said first and second frequency spectra are taken from the same sample volume of said blood flow.

75. The method of claim 62 further including the step of generating a modified frequency spectrum having a plurality of frequency components each of which is a composite of related frequency components of at least two frequency spectra obtained at different times, and wherein at least one of the frequency components that is used to detect an embolus is a frequency component from said modified frequency spectrum.

76. The method of claim 62 wherein said ultrasound reflections are processed from different locations in said blood flow thereby detecting the presence of an embolus at two different locations in said blood flow.

77. The method of claim 62 wherein said ultrasound is reflected from said blood flow at two spaced apart locations, and wherein said method further includes the steps of generating a respective frequency spectrum from the ultrasound reflections at each of said locations, and detecting the presence of an embolus at each of said locations as a function of a relationship between the amplitude of one frequency component and the amplitude of another frequency component in each of said frequency spectra thereby detecting the presence of an embolus at two different locations in said blood flow.

78. The method of claim 77 wherein said reflected ultrasound is reflected from respective ultrasound sources having different frequencies.

79. The method of claim 62 wherein said frequency component obtained at said first time is at a different frequency from said frequency component obtained at said different time.

80. A method of ultrasonically detecting an embolus in a blood flow, said method comprising:
reflecting ultrasound from ultrasound scatterers in said blood flow;
generating at least one ultrasound frequency spectrum indicative of the frequency of said reflected ultrasound, each frequency spectrum containing a plurality of frequency components indicative of the velocity of ultrasound scatterers in said blood flow;
comparing the frequency components in a spectrum to a predetermined value that is a function of the amplitude of a frequency component in a second spectrum obtained at a time after the other of said spectrums was obtained;
using a frequency component bearing a predetermined relationship to the frequency components being compared to said predetermined value to determine said predetermined value; and
using said frequency components to detect said embolus only if said frequency components exceed said predetermined value.

81. A method of ultrasonically detecting an embolus in a blood flow, said method comprising:
reflecting ultrasound from ultrasound scatterers in said blood flow;
generating at least one ultrasound frequency spectrum indicative of the frequency of said reflected ultrasound, each frequency spectrum containing a plurality of frequency components indicative of the velocity of ultrasound scatterers in said blood flow; and
detecting the presence of an embolus in said blood only if the amplitude of one frequency component is greater than a predetermined value and the amplitude of a second frequency component is less than a predetermined value.

82. The method of claim 81 wherein said predetermined value for each frequency component in said spectrum is determined as a function of the amplitudes of the same frequency component in a plurality of spectra obtained at an earlier point in time.

83. The method of claim 81 further including the step of comparing a plurality of frequency component pairs to said predetermined value and counting the number of times that one frequency component in each pair is greater than said predetermined value and the amplitude of the other frequency component in said pair is less than said predetermined value, said method further including the step of detecting an embolus only if said count is greater than a predetermined value.

84. The method of claim 81 wherein said predetermined value is a function of the amplitude of at least one frequency component in a second spectrum taken at a time that is different from when the other of said spectrum was obtained.

85. The method of claim 84 wherein said second spectrum is taken after the other of said spectrum was obtained.

86. A method of ultrasonically detecting an embolus in a blood flow, said method comprising:
reflecting ultrasound from ultrasound scatterers in said blood flow;
generating at least one ultrasound frequency spectrum indicative of the frequency of said reflected ultrasound, each frequency spectrum containing a plurality of frequency components indicative of the velocity of ultrasound scatterers in said blood flow; and
detecting the presence of an embolus in said blood as a function of a relationship between the amplitude of one frequency component and the amplitude of another frequency component;
generating a plurality of ultrasound frequency spectra indicative of the frequency of ultrasound having different respective frequencies reflected from ultrasound scatterers in said blood flow; and
determining a characteristic of a detected embolus as a function of a relationship between a frequency spectrum corresponding to reflected ultrasound of one frequency and a frequency spectrum corresponding to reflected ultrasound of another frequency.

87. The method of claim 86 wherein said ultrasound is reflected from ultrasound scatterers using a pulse Doppler unit operating at a plurality of different carrier frequencies, said pulse Doppler unit having the same pulse duration, pulse repetition rate, and depth gate for each of said carrier frequencies.

88. The method of claim 87 further including the steps of comparing the difference between said first and second composite values to a first predetermined value, and comparing the difference between said second and third composite values to a second predetermined value to determine the size of said embolus.

89. The method of claim 86 wherein said characteristic is determined as a function of a relationship between the power of one frequency spectrum and the power of another frequency spectrum.

90. The method of claim 89 wherein said characteristic is determined as a function of a relationship between the power of only a portion of said one frequency spectrum and the power of only a portion of said other the frequency spectrum.

91. The method of claim 89 further including the steps of:
determining a set of first intermediate values, each value in said set corresponding to the power of a respective frequency spectrum corresponding to ultrasound reflected from blood and an embolus in said blood flow;
determining a set of second intermediate values, each value in said set corresponding to the power of a respective frequency spectrum corresponding to ultrasound reflected from said blood flow;
calculating a set of composite values each of which is a function of the first and second intermediate values determined from the same frequency spectrum; and
examining a relationship between at least two of said composite values in said set to determine a characteristic of said embolus.

92. The method of claim 91 wherein each of said sets contain three values, and wherein said method further includes the steps of examining a relationship between two of said composite values and the relationship between one of said two composite values and the remaining composite value to identify said characteristic of said embolus.

93. The method of claim 91 wherein each of said sets contain three values, and wherein said method further includes the steps of determining the first of said composite values from the frequency spectrum of ultrasound reflected from said scatterers having the highest frequency, determining the third of said composite values from the frequency spectrum of ultrasound reflected from said scatterers having the lowest frequency, and determining the second of said composite values from the frequency spectrum of ultrasound reflected from said scatterers having an intermediate frequency.

94. The method of claim 91 further including the steps of comparing the difference between said first and second composite values to a first predetermined value, and comparing the difference between said second and third composite values to a second predetermined value to a determine the composition of said embolus.

95. The method of claim 86 wherein the characteristic of said detected embolus that is determined is the size of said embolus.

96. The method of claim 86 wherein the characteristic of said detected embolus that is determined is the composition of said embolus.

97. The method of claim 86 further including the step of scaling the frequency of the components in two of said frequency spectra as a function of the relative frequencies of ultrasound reflected from said scatterers so that the Doppler frequencies of ultrasound are scaled to the same velocity value responsive to scatters in said blood moving at the same velocity.

98. A method for determining a characteristic of an embolus in a blood flow, said method comprising:
generating a plurality of ultrasound frequency spectra indicative of the frequency of ultrasound having different respective frequencies reflected from ultrasound scatterers in said blood flow; and
determining a characteristic of a detected embolus as a function of a relationship between on frequency spectrum and another frequency spectrum.

99. The method of claim 98 wherein 3 different ultrasound frequency spectra indicative of the frequency of the reflection of 3 different respective ultrasound frequencies are generated, and wherein said characteristic is determined as a function of a relationship between all three of said frequency spectra.

100. The method of claim 98 wherein said characteristic is determined as a function of a relationship between the power of one frequency spectrum and the power of another frequency spectrum.

101. The method of claim 100 wherein said characteristic is determined as a function of a relationship between the power of only a portion of said one frequency spectrum and the power of only a portion of said other the frequency spectrum.

102. The method of claim 100 further including the steps of:
determining a set of first intermediate values, each value in said set corresponding to the power of a respective frequency spectrum corresponding to ultrasound reflected from blood and an embolus in said blood flow;
determining a set of second intermediate values, each value in said set corresponding to the power of a respective frequency spectrum corresponding to ultrasound reflected from said blood flow;
calculating a set of composite values each of which is a function of the first and second intermediate values determined from the same frequency spectrum; and
examining a relationship between at least two of said composite values in said set to determine a characteristic of said embolus.

103. The method of claim 102 wherein each of said sets contain three values, and wherein said method further includes the steps of examining a relationship between two of said composite values and the relationship between one of said two composite values and the remaining composite value to identify said characteristic of said embolus.

104. The method of claim 102 wherein each of said sets contain three values, and wherein said method further includes the steps of determining the first of said composite values from the frequency spectrum of ultrasound reflected from said scatterers having the highest frequency, determining the third of said composite values from the frequency spectrum of ultrasound reflected from said scatterers having the lowest frequency, and determining the second of said composite values from the frequency spectrum of ultrasound reflected from said scatterers having an intermediate frequency.

105. The method of claim 102 further including the steps of comparing the difference between said first and second composite values to a first predetermined value, and comparing the difference between said second and third composite values to a second predetermined value to determine the size of said embolus.

106. The method of claim 102 further including the steps of comparing the difference between said first and second composite values to a first predetermined value, and comparing the difference between said second and third composite values to a second predetermined value to determine the composition of said embolus.

107. The method of claim 98 further including the step of scaling the frequency of the components in two of said frequency spectra as a function of the relative frequencies of ultrasound reflected from said scatterers so that the Doppler frequencies of ultrasound are scaled to the same velocity value responsive to scatters in said blood moving at the same velocity.

108. The method of claim 98 wherein said first and second frequency spectra are taken from the same sample volume of said blood flow.

109. The method of claim 98 wherein said embolus is detected as a function of the relationship between the amplitude of a frequency component in a first frequency spectrum and the amplitude of a frequency component in a second frequency spectrum obtained at a time that is different from when said first frequency spectrum was obtained.

110. The method of claim 98 wherein the characteristic of said detected embolus that is determined is the size of said embolus.

111. The method of claim 98 wherein the characteristic of said detected embolus that is determined is the composition of said embolus.

112. The method of claim 98 further including the step of generating a modified frequency spectrum having a plurality of frequency components each of which is a composite of related frequency components of at least two frequency spectra obtained at different times, and wherein at least one of the frequency components that is used to detect an embolus is a frequency component from said modified frequency spectrum.

* * * * *

UNITED STATES PATENT AND TRADEMARK OFFICE
CERTIFICATE OF CORRECTION

PATENT NO. : 5,348,015

DATED : September 20, 1994

INVENTOR(S) : Mark A. Moehring, et al

It is certified that error appears in the above-indentified patent and that said Letters Patent is hereby corrected as shown below:

In column 23, claim 1, line 50, please delete "scatters" and substitute therefor --scatterers--.

In column 23, claim 1, line 59, please delete the second occurring "a".

In column 25, claim 12, line 7, please delete "scatters" and substitute therefor --scatterers--.

In column 25, claim 13, line 24, please delete "provides" and substitute therefor --provide--.

In column 25, claim 14, line 34, please delete "scatters" and substitute therefor --scatterers--.

In column 26, claim 19, line 27, after "has" and before "predetermined", please insert --a--.

In column 26, claim 20, line 40, please delete "scatters" and substitute therefor --scatterers--.

In column 26, claim 20, line 50, please delete "comprising" and substitute therefor --comparing--.

In column 27, claim 27, line 48, after "frequency" and before "spectrum", please delete --,--.

In column 28, claim 34, line 32, please delete "scatters" and substitute therefor --scatterers--.

In column 29, claim 40, line 9, please delete "position" and substitute therefor --positioned--.

In column 29, claim 40, line 15, please delete "scatters" and substitute therefor --scatterers--.

In column 31, claim 52, line 4, please delete "scatters" and substitute therefor --scatterers--.

In column 31, claim 54, line 14, please delete "40" and substitute therefor --41--.

In column 31, claim 54, line 16, please delete "doppler" and substitute therefor --Doppler--.

In column 32, claim 62, line 5, please delete "scatters" and substitute therefor --scatterers--.

UNITED STATES PATENT AND TRADEMARK OFFICE
CERTIFICATE OF CORRECTION

PATENT NO. : 5,348,015
DATED : September 20, 1994
INVENTOR(S) : Mark A. Moehring, et al It is certified that error appears in the above-indentified patent and that said Letters Patent is hereby corrected as shown below:

In column 32, claim 64, line 18, please delete "amplitude" and substitute therefor --amplitudes--.

In column 32, claim 64, line 20, please delete "provides" and substitute therefor --provide--.

In column 32, claim 66, line 38, please delete "80" and substitute therefor --62--.

In column 36, claim 97, line 6, please delete "scatters" and substitute therefor --scatterers--.

In column 37, claim 107, line 18, please delete "scatters" and substitute therefor --scatterers- Signed and Sealed this Seventeenth Day of October, 1995

*Attest:*

BRUCE LEHMAN

*Attesting Officer*    Commissioner of Patents and Trademarks